United States Patent [19]

Sakata et al.

[11] Patent Number: 5,476,597
[45] Date of Patent: Dec. 19, 1995

[54] LIQUID SOFTENER COMPOSITION, NOVEL QUATERNARY AMMONIUM SALT, AND PROCESS FOR THE PREPARATION OF SAID SALT

[75] Inventors: Yushi Sakata; Junichi Inokoshi; Tohru Katoh; Osamu Tachizawa; Uichiro Nishimoto; Yasuki Ohtawa; Masaaki Yamamura, all of Wakayama, Japan

[73] Assignee: Kao Corporation, Tokyo, Japan

[21] Appl. No.: 302,213

[22] Filed: Sep. 8, 1994

[30] Foreign Application Priority Data

Sep. 10, 1993 [JP] Japan ................................ 5-225964
Sep. 22, 1993 [JP] Japan ................................ 5-236171
Sep. 22, 1993 [JP] Japan ................................ 5-236172
Mar. 17, 1994 [JP] Japan ................................ 6-047094

[51] Int. Cl.$^6$ .................................................. D06M 13/46
[52] U.S. Cl. ........................... 252/8.8; 252/8.6; 252/8.9; 554/52
[58] Field of Search ...................... 252/8.6, 8.8, 8.9; 554/52

[56] References Cited

U.S. PATENT DOCUMENTS

| | | | |
|---|---|---|---|
| 4,370,272 | 1/1983 | Wechsler et al. | 260/404 |
| 5,282,983 | 2/1994 | Yamamura et al. | 252/8.6 |

FOREIGN PATENT DOCUMENTS

| | | |
|---|---|---|
| 1163275 | 3/1984 | Canada . |
| 0021431 | 1/1981 | European Pat. Off. . |
| 025165 | 3/1981 | European Pat. Off. . |
| 0192145 | 8/1986 | European Pat. Off. . |
| 267551 | 5/1988 | European Pat. Off. . |
| 472178 | 2/1992 | European Pat. Off. . |
| 0472178 | 2/1992 | European Pat. Off. . |
| 348190 | 12/1977 | France . |
| 4135115 | 4/1993 | Germany . |
| 5230001 | 9/1993 | Japan . |
| 6116220 | 4/1994 | Japan . |
| WO9117975 | 11/1991 | WIPO . |

OTHER PUBLICATIONS

English Language Abstract German Patent No. DE 4135115 Apr. 29, 1993.
English Language Abstract of EPA Patent No. 0 025 165 Mar. 18, 1981.
English Language Abstract of French Patent No. 2348 190 Dec. 16, 1977.
English Language Abstract of EPA Patent No. 0267 551 May 18, 1988.

*Primary Examiner*—Paul Lieberman
*Assistant Examiner*—Michael Tierney
*Attorney, Agent, or Firm*—Birch, Stewart, Kolasch & Birch

[57] ABSTRACT

To provide an aqueous fabric softener composition, which is excellent in softening performance, elasticity and storage stability, and a quaternary ammonium salt which is useful as a softening base of this composition and nondetrimental to the natural environment because of its excellent biodegradability and a process for the preparation of this salt.

The aqueous fabric softener composition of the present invention comprises from 3 to 40% by weight of a quaternary ammonium salt represented by the following formula (I), and water:

$$\begin{array}{c} R^1 \quad\quad C_2H_4OCOR^3 \\ \diagdown \ _+ \diagup \\ N \quad\quad X^- \\ \diagup \quad\quad \diagdown \\ R^2 \quad\quad C_2H_4NHCOR^4 \end{array} \quad (I)$$

wherein $R^1$ and $R^2$ represent each a $C_{1-4}$ alkyl group, etc.; $R^3$ and $R^4$ represent each a $C_{7-35}$ alkyl group, etc.; and $X^-$ represents an anion group.

13 Claims, No Drawings

LIQUID SOFTENER COMPOSITION, NOVEL QUATERNARY AMMONIUM SALT, AND PROCESS FOR THE PREPARATION OF SAID SALT

BACKGROUND OF THE INVENTION

1. Field of the Invention

The present invention relates to an aqueous fabric softener composition, i.e., a liquid softener composition, which can impart an excellent softness and elasticity (fluffiness) to various fibers, and is excellent in storage stability over a wide range of temperature. Further, the present invention relates to a quaternary ammonium salt which is useful as a base of the above-mentioned aqueous fabric softener composition and is nondetrimental to the natural environment because of its excellent biodegradability, and a process for the preparation thereof. Furthermore, the present invention relates to a use of the quaternary ammonium salt, and a method for imparting softness and elasticity to fibers which comprises using the quaternary ammonium salt.

2. Description of the Related Art

Fabric softeners for domestic use at the present time are generally in the form of a composition comprising di(hardened beef tallow alkyl)dimethylammonium chloride as the main component. The reason this quaternary ammonium salt is used as the main component in fabric softeners for domestic use is that the salt exerts an excellent softening effect on various fibers even when used in a small amount.

Although the above-mentioned quaternary ammonium salt exerts an excellent softening effect, it sometimes deteriorates the elasticity of fibers, in particular, cotton and thus imparts an oily hand to the fabrics when applied at a high concentration in order to further elevate the softening effect. Further, when stored for a long period of time, a fabric softener composition comprising the above-mentioned quaternary ammonium salt is easily thickened, gels or separates out in some cases due to its physicochemical properties.

Furthermore, there is a disadvantage that a quaternary ammonium salt having two long-chain alkyl groups, such as the above-mentioned di(hardened beef tallow alkyl)dimethylammonium chloride, has poor biodegradability.

Attempts have been made to eliminate or reduce these disadvantages of the conventional fabric softeners for domestic use and the conventional quaternary ammonium salts, which is a main component of the fabric softeners, by introducing an ester group or an amido group between a quaternary nitrogen atom and a long-chain alkyl group. For example, European Patent Publication-A No. 472,178 (published on Feb. 26, 1992) and U.S. Pat. No. 5,282,983 (assignee: Kao Corp.; date of patent: Feb. 1, 1994) corresponding hereto have disclosed a fabric softener composition comprising a di(long-chain alkyl) quaternary ammonium salt having ester and amido groups, which imparts an oily hand to the clothes treated therewith. Further, European Patent Publication-A No. 192,145 (published on Aug. 27, 1986) has disclosed a fabric softener composition comprising a di(long-chain alkyl) quaternary ammonium salt having ester and amido groups, which is highly dispersible in cold water without gelling.

Meanwhile, attempts have also been made to improve the storage stability of the fabric softener compositions comprising a quaternary ammonium salt with the use of an additive. Namely, in addition to the above-mentioned quaternary ammonium salt, various additives, such as polyoxyethylene-based nonionic surfactants, electrolytes and solvents, are employed in marketed softeners for domestic use so as to improve the storage stability to thereby keep them stable for a long period of time.

European Patent Publication-A No. 21,431 (published on Jan. 7, 1981) has disclosed a diester type quaternary ammonium salt as a base for fabric softeners that do not utilize di(long-chain alkyl) quaternary ammonium salts. However, the diester type quaternary ammonium salt is still unsatisfactory in both biodegradability and softening performance.

As described above, fabric softener compositions comprising a quaternary ammonium salt in the prior art are still unsatisfactory in softening performance, storage stability and biodegradability.

Accordingly, it is an object of the present invention to provide an aqueous fabric softener composition which shows a fully satisfactory performance in softening effect, elasticity (fluffiness) and storage stability, and to provide a quaternary ammonium salt which is suitable to incorporate into such an aqueous fabric softener composition, useful as a softener base and nondetrimental to the natural environment because of its excellent biodegradability, and a process for the preparation of this salt. Further, an object of the present invention is to provide a use of the quaternary ammonium salt, and to provide a method for imparting softness and elasticity to fibers which comprises using the quaternary ammonium salt.

DISCLOSURE OF THE INVENTION

SUMMARY OF THE INVENTION

The present inventors have conducted extensive studies to attain the above objects. As the result, they found that the above-mentioned objects can be attained by using an aqueous fabric softener composition comprising a quaternary ammonium salt of a highly specified structure, thus completing the present invention.

Accordingly, the present invention provides an aqueous fabric softener composition comprising 3 to 40% by weight, based on the total weight of the composition of component (A) consisting of at least one quaternary ammonium salt selected from the group consisting of compounds represented by the following formulas (I) and (II), and water:

(I)

wherein $R^1$ and $R^2$ may be the same or different from each other and each represents an alkyl or hydroxyalkyl group having 1 to 4 carbon atoms; $R^3$ and $R^4$ may be the same or different from each other and each represents a linear or branched alkyl or alkenyl group having 7 to 35 carbon atoms; and $X^-$ represents an anion group; and

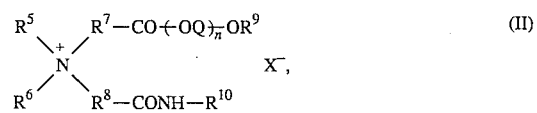
(II)

wherein $R^5$ and $R^6$ may be the same or different from each other and each represents an alkyl or hydroxyalkyl group having 1 to 4 carbon atoms; $R^7$ and $R^8$ may be the same or different from each other and each represents an alkylene, alkenylene or hydroxyalkylene group having 1 to 5 carbon atoms; $R^9$ and $R^{10}$ may be the same or different from each other and each represents a linear or branched alkyl or alkenyl group having 8 to 36 carbon atoms; Q represents an alkylene group having 2 to 6 carbon atoms; $X^-$ represents an anion group; n is a number of from 0 to 10; and each of Q's may be the same or different from one another.

It is preferable that a quaternary ammonium salt represented by the above formula (II), or a mixture of a quaternary ammonium salt represented by the above formula (I) and a quaternary ammonium salt represented by the above formula (II) is used as component (A).

It is preferable that a quaternary ammonium salt represented by the above formula (I), or a quaternary ammonium salt represented by the above formula (II) in which Q is a group represented by the formula:

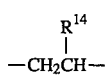

or the formula:

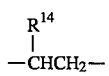

(wherein $R^{14}$ represents a hydrogen atom or an alkyl group having 1 to 4 carbon atoms) is used.

As the aqueous fabric softener composition according to the present invention, the following embodiments are preferable:

(1) a composition further comprising a linear or branched, saturated or unsaturated fatty acid having 8 to 36 carbon atoms as component (B), wherein the amount of component (B) is not more than 100% by weight based on the weight of component (A), (2) a composition further comprising a monohydric alcohol having 1 to 4 carbon atoms as component (C), wherein the amount of component (C) is not more than 60% by weight based on the weight of component (A), (3) a composition further comprising not more than 40% by weight, based on the total weight of the composition, of a quaternary ammonium salt represented by the following formula (III) as component (D), wherein the total amount of components (A) and (D) is from 3 to 50% by weight based on the total weight of the composition:

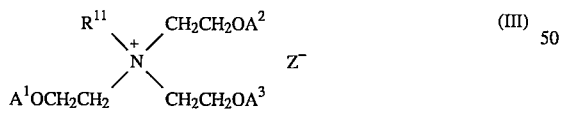

wherein $R^{11}$ represents an alkyl or hydroxyalkyl group having 1 to 4 carbon atoms; $A^1$, $A^2$ and $A^3$ may be the same or different from one another and each represents a hydrogen atom or a group represented by the formula: $R^{12}CO$— (wherein $R^{12}$ represents a linear or branched alkyl or alkenyl group having 7 to 35 carbon atoms), and at least one of $A^1$, $A^2$ and $A^3$ is a group represented by the formula: $R^{12}CO$— (wherein $R^{12}$ is as defined above); and $Z^-$ represents an anion group, (4) a composition further comprising 0.5 to 5% by weight, based on the total weight of the composition, of a polyether compound having a weight average molecular weight of from 5,000 to 2,000,000 which is obtained by adding ethylene oxide and, if necessary, at least one of propylene oxide and trimethylene oxide to a compound having at least 3 active hydrogen atoms, wherein the ratio of the oxyethylene groups is 55% by weight or more based on the molecular weight of the polyether compound, or a derivative thereof, as component (E), wherein the weight ratio of component (E) to component (A) is from 1/100 to 1/2.5, and the total amount of components (A) and (E) is from 4 to 45% by weight based on the total weight of the composition.

(5) a composition further comprising an amidoamine represented by the following formula (IV) or an acid salt thereof as component (F), wherein the amount of component (F) is not more than 110% by weight based on the weight of component (A):

wherein $R^5$, $R^6$, $R^8$ and $R^{10}$ are each as defined above, and (6) a composition further comprising at least one compound selected from the group consisting of compounds represented by the following formulas (XVII-1) to (XVII-9) as component (G):

wherein $R^{15}$ and $R^{16}$ may be the same or different from each other and each represents a linear or branched, alkyl, alkenyl or 2-hydroxyalkyl group having 10 to 24 carbon atoms; $R^{17}$ represents an alkyl or hydroxyalkyl group having 1 to 3 carbon atoms, a benzyl group or a group represented by the formula: —$(C_2H_4O)_mH$ (wherein m is a number of from 1 to 3); $R^{18}$ represents a hydrogen atom, an alkyl or hydroxyalkyl group having 1 to 3 carbon atoms, a benzyl group or a group represented by the formula: —$(C_2H_4O)_mH$ (wherein m is as defined above); and $Z^-$ is as defined above,

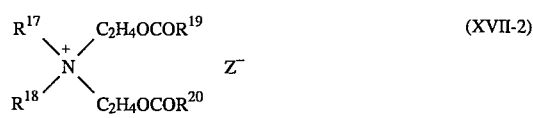

wherein $R^{17}$, $R^{18}$ and $Z^-$ are each as defined above; and $R^{19}$ and $R^{20}$ may be the same or different from each other and each represents a linear or branched alkyl, alkenyl or 2-hydroxyalkyl group having 9 to 23 carbon atoms,

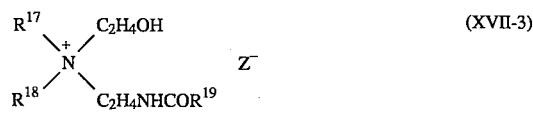

wherein $R^{17}$, $R^{18}$, $R^{19}$ and $Z^-$ are each as defined above, $$\begin{array}{c} R^{18} \\ | \\ N-CH_2 \\ R^{19}-C^+ \quad | \quad Z^- \\ \diagdown \\ N-CH_2 \\ | \\ C_2H_4-B-R^{20} \end{array} \quad \text{(XVII-4)}$$

wherein $R^{18}$, $R^{19}$, $R^{20}$ and $Z^-$ are each as defined above; and B represents a group represented by the formula: —OCO— or the formula: —NHCO—, $$\begin{array}{c} R^{18} \quad CH_2CH_2-B-R^{20} \\ \diagdown + \diagup \\ N-CH_2 \\ R^{19}-C \quad | \quad Z^- \\ \diagdown\diagdown \\ N-CH_2 \end{array} \quad \text{(XVII-5)}$$

wherein $R^{18}$, $R^{19}$, $R^{20}$, B and $Z^-$ are each as defined above, $$\begin{array}{c} R^{19}COOCH_2 \\ | \\ CHOH \\ | \\ CH_2OH \end{array} \quad \text{(XVII-6)}$$

wherein $R^{19}$ is as defined above, $$R^{19}CON\begin{array}{c} \diagup C_2H_4OH \\ \diagdown C_2H_4NHCOR^{20} \end{array} \quad \text{(XVII-7)}$$

wherein $R^{19}$ and $R^{20}$ are each as defined above, $$R^{19}CON\begin{array}{c} \diagup C_2H_4OCOR^{21} \\ \diagdown C_2H_4NHCOR^{20} \end{array} \quad \text{(XVII-8)}$$

wherein $R^{19}$ and $R^{20}$ are each as defined above; and $R^{21}$ represents a linear or branched, alkyl, alkenyl or 2-hydroxyalkyl group having 9 to 23 carbon atoms, and $$R^{22}OH \quad \text{(XVII-9)}$$

wherein $R^{22}$ represents a linear or branched, alkyl or alkenyl group having 10 to 24 carbon atoms.

Further, the following embodiments are preferable as the aqueous fabric softener composition according to the present invention when component (A) is the quaternary ammonium salt represented by the above formula (I):

(7) a composition further comprising a quaternary ammonium salt represented by the following formula (XX) as component (H), wherein the amount of component (H) is not more than 110% by weight based on the weight of the component (A):

$$\begin{array}{c} R^1 \quad C_2H_4OH \\ \diagdown + \diagup \\ N \quad X^- \\ \diagup \diagdown \\ R^2 \quad C_2H_4NHCOR^4 \end{array} \quad \text{(XX)}$$

wherein $R^1$, $R^2$, $R^4$ and $X^-$ are each as defined above, (8) a composition further comprising a linear or branched, saturated or unsaturated fatty acid having 8 to 36 carbon atoms as component (B), wherein the amount of component (B) is not more than 100% by weight based on the weight of component (A), and (9) a composition further comprising a monohydric alcohol having 1 to 4 carbon atoms as component (C), wherein the amount of component (C) is not more than 60% by weight based on the weight of component (A).

The following embodiments are preferable as the aqueous fabric softener composition according to the present invention when component (A) is the quaternary ammonium salt represented by the above formula (II) in which Q is a group represented by the formula:

$$\begin{array}{c} R^{14} \\ | \\ -CH_2CH- \end{array}$$

or the formula:

$$\begin{array}{c} R^{14} \\ | \\ -CHCH_2- \end{array}$$

(wherein $R^{14}$ represents a hydrogen atom or an alkyl group having 1 to 4 carbon atoms):

(10) a composition further comprising an amidoamine represented by the following formula (IV) or an acid salt thereof as component (F), wherein the amount of component (F) is not more than 110% by weight based on the weight of component (A):

$$\begin{array}{c} R^5 \\ \diagdown \\ N-R^8-CONH-R^{10} \\ \diagup \\ R^6 \end{array} \quad \text{(IV)}$$

wherein $R^5$, $R^6$, $R^8$ and $R^{10}$ are each as defined above, and

(11) a composition further comprising a monohydric alcohol having 1 to 4 carbon atoms as component (C), wherein the amount of component (C) is not more than 60% by weight based on the weight of component (A).

Further, the present invention provide a quaternary ammonium salt represented by the following formula (II) which is suitable to incorporate into the above softener composition as a softening base:

$$\begin{array}{c} R^5 \quad R^7-CO+OQ\overline{)_n}OR^9 \\ \diagdown + \diagup \\ N \quad X^- \\ \diagup \diagdown \\ R^6 \quad R^8-CONH-R^{10} \end{array} \quad \text{(II)}$$

wherein $R^5$, $R^6$, $R^7$, $R^8$, $R^9$, $R^{10}$, Q, $X^-$ and n are each as defined above.

Among quaternary ammonium salts represented by the above formula (II), the following ones are preferable:

(a) a quaternary ammonium salt represented by the above formula (II), wherein $R^5$ and $R^6$ represent each an alkyl or hydroxyalkyl group having 1 or 2 carbon atoms, $R^7$ and $R^8$ represent each an alkylene group having 1 or 2 carbon atoms, Q represents an alkylene group having 2 or 3 carbon atoms, $R^9$ and $R^{10}$ represent each an alkyl or alkenyl group having 12 to 22 carbon atoms, n is a number of 0 or 1 to 5, and $X^-$ is $Cl^-$, (b) a quaternary ammonium salt represented by the above formula (II), wherein $R^5$ and $R^6$ represent each a methyl group, $R^7$ and $R^8$ represent each an alkylene group having 1 or 2 carbon atoms, Q is an ethylene group, $R^9$ and $R^{10}$ represent each an alkyl or alkenyl group having 12 to 22 carbon atoms, n is a number of 0 or 1 to 5, and $X^-$ is $Cl^-$, (c) a quaternary ammonium salt represented by the above formula (II), wherein Q is a group represented by the formula:

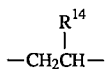

or the formula:

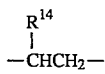

(wherein $R^{14}$ represents a hydrogen atom or an alkyl group having 1 to 4 carbon atoms), and n is 0 or an integer of 1 to 10, (d) a quaternary ammonium salt represented by the above formula (II) wherein $R^5$ and $R^6$ represent each an alkyl or hydroxyalkyl group having 1 or 2 carbon atoms, $R^7$ and $R^8$ represent each an alkylene group having 1 or 2 carbon atoms, Q is a group represented by the formula:

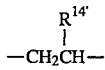

or the formula:

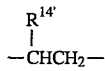

(wherein $R^{14'}$ represents a hydrogen atom or a methyl group), $R^9$ and $R^{10}$ represent each an alkyl or alkenyl group having 12 to 22 carbon atoms, n is 0 or an integer of 1 to 5, and $X^-$ is $Cl^-$, and (e) a quaternary ammonium salt represented by the above formula (II), herein $R^5$ and $R^6$ represent each a methyl group, $R^7$ and $R^8$ represent each an alkylene group having 1 or 2 carbon atoms, Q is an ethylene group, $R^9$ and $R^{10}$ represent each an alkyl or alkenyl group having 12 to 22 carbon atoms, n is 0 or an integer of 1 to 5, and $X^-$ is $Cl^-$.

Among quaternary ammonium salts represented by the above formula (II), the following one is the most preferable:

(f) a quaternary ammonium salt represented by the above formula (II), wherein $R^5$ and $R^6$ represent each a methyl group, $R^7$ and $R^8$ represent each an alkylene group having 1 or 2 carbon atoms, $R^9$ and $R^{10}$ represent each an alkyl or alkenyl group having 16 to 18 carbon atoms, n is 0 and $X^-$ is $Cl^-$.

The present invention provides a process for the preparation of the quaternary ammonium salt represented by the above formula (II), which comprises the steps of reacting an amino ester represented by the formula (V):

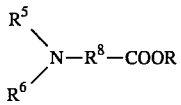

(wherein $R^5$, $R^6$ and $R^8$ are each as defined above; and R represents an alkyl group having 1 to 3 carbon atoms) with an amine represented by the formula (VI): $R^{10}$—$NH_2$ (VI) (wherein $R^{10}$ is as defined above) to thereby give an amidoamine represented by the formula (IV):

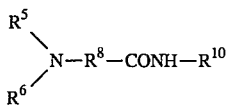

(wherein $R^5$, $R^6$, $R^8$ and $R^{10}$ are each as defined above), and then reacting the amidoamine with a compound represented by the formula (VII): Y—$R^7$—CO—(O—)$_n$—$OR^9$ (VII) (wherein $R^7$, R9, Q and n are each as defined above; and Y represents a halogen atom).

The process may further comprise a step of exchanging the counter ion of the quaternary ammonium salt obtained.

Further, the present invention provides a process for the preparation of a quaternary ammonium salt represented by the above formula (I), which comprises the steps of reacting an amine represented by the formula (VIII):

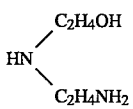

with a fatty acid represented by the formula (IX): $R^4COOH$ (IX) (wherein $R^4$ is as defined above) to thereby give an imidazoline represented by the formula (X):

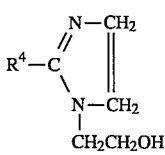

(wherein $R^4$ is as defined above), subjecting the imidazoline thus obtained to ring-opening reaction through hydrolysis to thereby give an amine represented by the formula (XI):

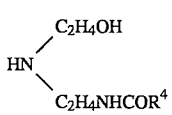

(wherein $R^4$ is as defined above), reacting the amine with an aldehyde represented by the formula (XII): $R^{13}CHO$ (XII) (wherein $R^{13}$ represents a hydrogen atom or an alkyl or hydroxyalkyl group having 1 to 3 carbon atoms), reducing the product to give a tertiary amine amide represented by the formula (XIII):

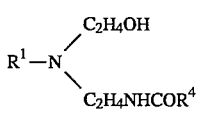

(wherein $R^1$ and $R^4$ are each as defined above), esterifying the tertiary amine amide with a fatty acid represented by the formula (XIV): $R^3COOH$ (XIV) (wherein $R^3$ is as defined above) or a lower alkyl ester thereof, preferably a fatty acid (XIV), to thereby give a tertiary amine amide ester represented by the formula (XV):

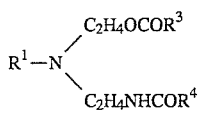
(XV)

(wherein $R^1$, $R^3$ and $R^4$ are each as defined above), and then quaternizing the tertiary amine amide ester with a quaternizing agent.

The process may further comprise a step of exchanging the counter ion of the quaternary ammonium salt obtained.

Among quaternary ammonium salts represented by the above formula (I), a quaternary ammonium salt represented by the above formula (I) wherein $R^1$ and $R^2$ represent each a methyl group, $R^3CO$ and $R^4CO$ represent each an acyl group derived from hardened beef tallow and $X^-$ is $Cl^-$ is the most preferable.

Furthermore, the present invention provides a use of a quaternary ammonium salt represented by the above formula (I) for imparting softness and elasticity to fibers, a use of a quaternary ammonium salt represented by the above formula (II) for imparting softness and elasticity to fibers, a method for imparting softness and elasticity to fibers, which comprises treating fibers with an aqueous solution containing an appropriate amount of a quaternary ammonium salt represented by the above formula (I), and a method for imparting softness and elasticity to fibers, which comprises treating fibers with an aqueous solution containing an appropriate amount of a quaternary ammonium salt represented by the above formula (II).

Further scope and applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

[Component (A)]

In the present invention, a quaternary ammonium salt represented by the above formula (I) [hereinafter referred to simply as a quaternary ammonium salt (I)], a quaternary ammonium salt represented by the above general formula (II) [hereinafter referred to simply as quaternary ammonium salt (II)] or a mixture thereof is used as component (A).

In the quaternary ammonium salt (I), $X^-$ represents an anion group. Examples of the anion group include halide anion groups, such as $Cl^-$ and $Br^-$, and alkyl ($C_1$ to $C_5$) sulfate groups, such as $CH_3SO_4^-$, $C_2H_5SO_4^-$ and $C_3H_7SO_4^-$.

Examples of the quaternary ammonium salt (I) are as follows:

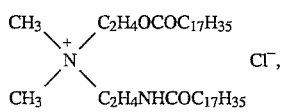

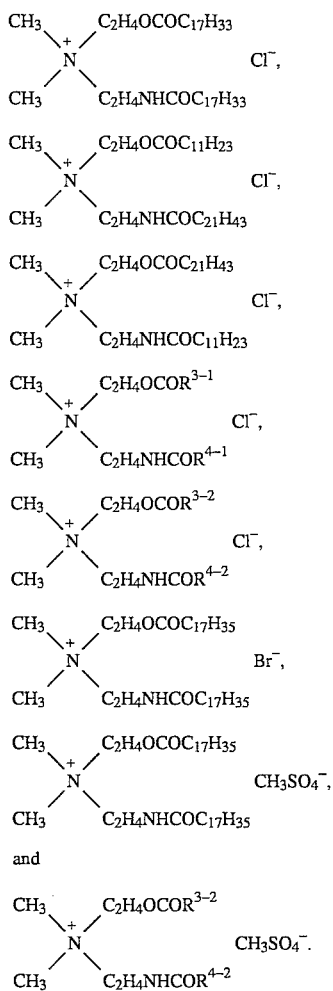

In the formulas cited above, $R^{3-1}$ and $R^{4-1}$ represent each an alkyl group obtained by eliminating a carboxyl group from hardened beef tallow fatty acid; and $R^{3-2}$ and $R^{4-2}$ represent each an alkyl group obtained by eliminating a carboxyl group from hardened palm oil fatty acid.

The quaternary ammonium salt (I) may be prepared, for example, in accordance with the following scheme:

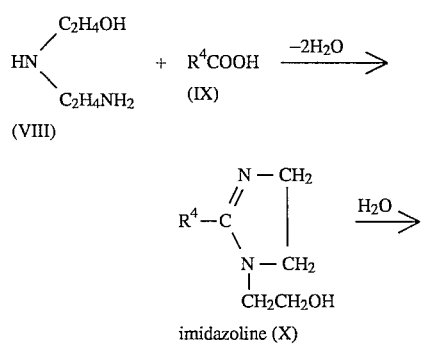

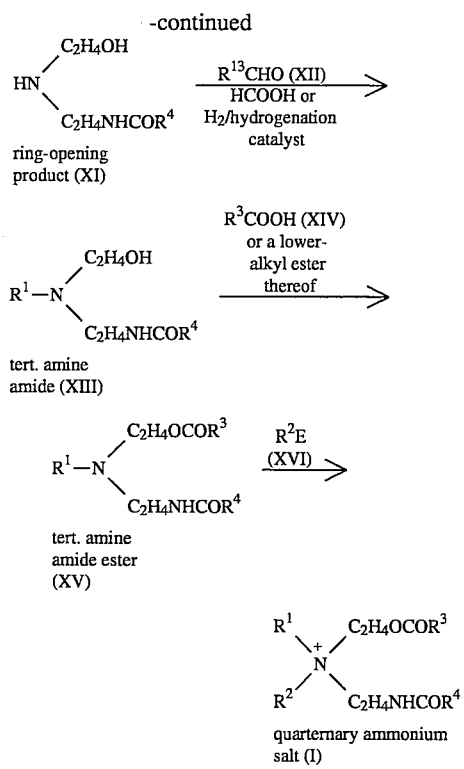

In the above formulas, $R^1$, $R^2$, $R^3$, $R^4$ and $X^-$ are each as defined above; $R^{13}$ represents a hydrogen atom or an alkyl or hydroxyalkyl group having 1 to 3 carbon atoms; and E represents a halogen atom or a group represented by the formula: $R^2SO_4$ (wherein $R^2$ is as defined above).

Namely, N-(2-aminoethyl)ethanolamine (VIII) is first reacted with a fatty acid (IX) to thereby give an imidazoline (X). In this step, the molar ratio of the N-(2-aminoethyl)ethanolamine (VIII) to the fatty acid (IX) is from 1.0 to 2.0, preferably from 1.1 to 1.5 and the reaction temperature is from 150° to 250° C., preferably from 180° to 230° C. It is desirable to slowly evacuate the reaction system from atmospheric pressure to about 5 Torr to thereby elevate the dehydration efficiency.

Examples of the fatty acid (IX) to be used herein include those originating from natural fats and oils such as coconut oil, palm oil, beef tallow, rapeseed oil and fish oil in general, though synthetic fatty acids having 8 to 36 carbon atoms are also usable therefore.

The imidazoline (X) thus obtained is then subjected to ring-opening reaction through hydrolysis in a mixed solvent such as water/ethanol or in water to thereby give a ring-opening product (XI). This reaction is effected with or without the use of a catalyst such as NaOH. Generally, the reaction temperature ranges from 80° to 140° C. and the reaction time is from 2 to 10 hours. In this step, water is used in an amount 1 to 10 times by mol, preferably 2 to 5 times by mol, as much as the imidazoline (X), and ethanol is used in an amount of from 0 to 50% by weight, preferably from about 10 to 30% by weight, based on the total weight of the imidazoline (X) and water. NaOH is used in an amount of from 0 to 10% by mol, preferably from 0 to 5% by mol, based on the imidazoline (X).

The ring-opening product (XI) thus obtained is reacted with an aldehyde (XII), such as formaldehyde and acetaldehyde under ordinary conditions and then the product is reduced to give a tert amine amide (XIII). When Leuckart reaction is employed in this step, the reduction is effected with formic acid. Specifically, an aldehyde (XII) or a 20 to 40% aqueous solution thereof is dropwise added to a ring-opening product (XI) in 0.5 to 5 hours at a temperature of 60° to 140° C. in the presence or absence of a solvent such as isopropanol and ethanol. Then, formic acid is dropwise added to the resulting mixture at that temperature, and the reaction is effected at that temperature for 1 to 20 hours. The aldehyde (XII) is used in an amount of from 0.8 to 1.5 mol, preferably from 1.0 to 1.2 mol, per mol of the ring-opening product (XI). The formic acid is used in an amount of from 0.8 to 1.5 mol, preferably from 1.0 to 1.2 mol, per mol of the ring-opening product (XI). When reductive alkylation is employed in this step, the reduction is effected with hydrogen in the presence of a hydrogenation catalyst. Specifically, an aldehyde (XII) or a 20 to 40% aqueous solution thereof is dropwise added to a ring-opening product (XI) in 0.1 to 5 hours at a temperature of 80° to 150° C. under a hydrogen pressure of 10 to 30 kg/cm²G in the presence or absence of a solvent such as isopropanol and ethanol in the presence of 0.1 to 5% of a catalyst such as Raney nickel and Pd/C. Then reaction is effected at that temperature under that hydrogen pressure for 1 to 10 hours. Alternatively, an aldehyde (XII) or a 20 to 40% aqueous solution thereof is dropwise added to a ring-opening product (XI) as described in the Leuckart reaction, a catalyst such as Raney nickel and Pd/C is added to the resulting mixture in an amount of from 0.1 to 54, and the reduction is effected under a hydrogen pressure of 10 to 30 kg/cm²G for 1 to 10 hours.

Then, this tert amine amide (XIII) is esterified with a fatty acid (XIV) or a lower alkyl ($C_1$ to $C_3$) ester thereof, preferably a fatty acid (XIV), to thereby give a tert. amine amide ester (XV). Examples of the fatty acid (XIV) to be used herein include those originating from natural fats and oils such as coconut oil, palm oil, beef tallow, rapeseed oil and fish oil in general, though synthetic fatty acids having 8 to 36 carbon atoms are also usable therefore. Examples of the lower alkyl group in the lower alkyl ester of the fatty acid (XIV) include methyl group, ethyl group and propyl group.

The tert. amine amide ester (XV) thus obtained is quaternized by a known method with the use of a quaternizing agent (XVI) to thereby give a quaternary ammonium salt (I). Examples of the quaternizing agent (XVI) include alkyl halides (for example, methyl chloride, ethyl chloride and methyl bromide) and dialkylsulfates (for example, dimetylsulfate and diethylsulfate). Specifically, an alkyl halide is reacted with a tert. amine amide ester (XV) at a temperature of from 60° to 120° C. for 2 to 10 hours in the presence or absence of a solvent such as isopropanol and ethanol. Alternatively, a dialkylsulfate is dropwise added to a tert. amine amide ester (XV) at a temperature of from 50° to 100° C. in 1 to 6 hours in the presence or absence of a solvent such as isopropanol and ethanol, and then the reaction is effected at that temperature for 1 to 10 hours. The alkyl halide is used in an amount of from 0.8 to 1.5 mol, preferably from 1.0 to 1.3 mol, per mol of the tert. amine amide ester (XV). The dialkylsulfate is used in an amount of from 0.8 to 1.5 mol, preferably from 0.9 to 1.0 mol, per mol of the tert. amine amide ester (XV).

The counter ion of the quaternary ammonium salt (I) thus obtained may be exchanged by using, for example, an ion exchange resin, if necessary. Needless to say, the quaternary ammonium salts obtained by effecting the counter ion exchange are also quaternary ammonium salts (I) according to the present invention.

The novel compound, quaternary ammonium salt (II) is also usable as component (A) in the present invention.

Specific examples of the $X^-$ group in the formula (II) include those cited in the case of the quaternary ammonium salt (I). In the formula (II), Q represents an alkylene group having 2 to 6 carbon atoms, and specific examples thereof include a group represented by the formula:

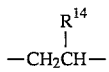

and a group represented by the formula:

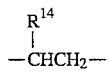

(wherein $R^{14}$ represents a hydrogen atom or an alkyl group having 1 to 4 carbon atoms). The formula (II) also represents a mixture of compounds wherein only the type and/or the addition mole number of the alkylene oxide added are/is different from one another, in addition to a single compound. Namely, n is also an average addition mole number of alkylene oxide. Each of Q's in the single compound or in each compound constituting the mixture may be the same or different from one another.

Examples of the quaternary ammonium salt (II) are as follows:

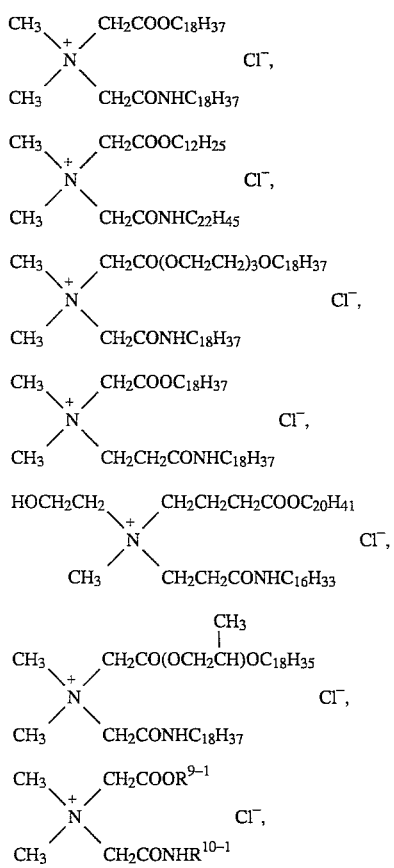

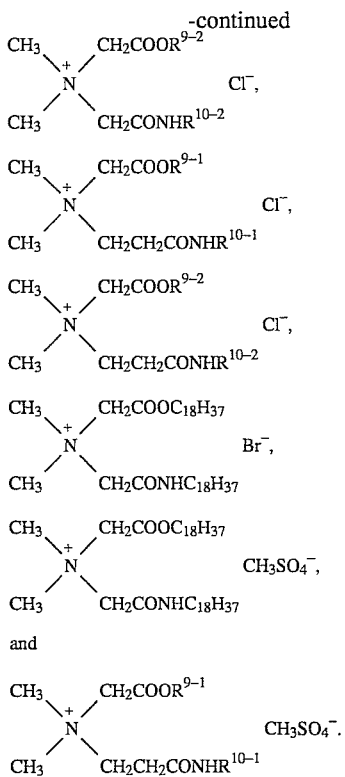

and

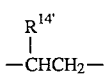

In the formulas cited above, $R^{9-1}$ and $R^{10-1}$ represent each an alkyl group obtained by substituting a methylene group for a carboxyl group of hardened beef tallow fatty acid; and $R^{9-2}$ and $R^{10-2}$ represent each an alkyl group obtained by substituting a methylene group for a carboxyl group of a hardened palm oil fatty acid.

Among the quaternary ammonium salts (II), preferable ones are compounds wherein $R^5$ and $R^6$ represent each an alkyl or hydroxyalkyl group having 1 or 2 carbon atoms, $R^7$ and $R^8$ represent each an alkylene group having 1 or 2 carbon atoms, Q is a group represented by the formula:

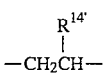

or the formula:

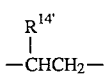

(wherein $R^{14'}$ represents a hydrogen atom or a methyl group); $R^9$ and $R^{10}$ represent each an alkyl or alkenyl group having 12 to 22 carbon atoms, n is 0 or an integer of 1 to 5 and $X^-$ is $Cl^-$. Among these compounds, still preferable ones are those wherein $R^5$ and $R^6$ are methyl groups, $R^7$ and $R^8$ are each an alkylene group having 1 or 2 carbon atoms and Q is an ethylene group.

The quaternary ammonium salt (II) may be prepared, for example, in accordance with the following scheme.

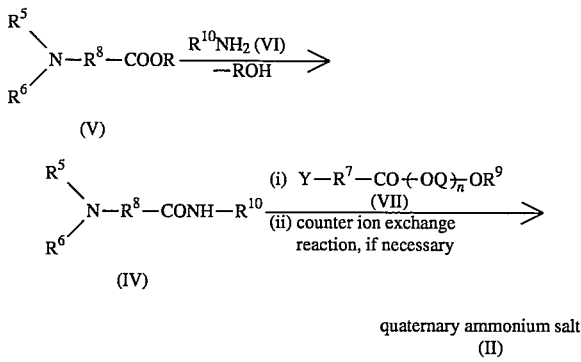

quaternary ammonium salt
(II)

In the above formula, $R^5$, $R^6$, $R^7$, $R^8$, $R^9$, $R^{10}$, Q and n are each as defined above; R represents an alkyl group having 1 to 3 carbon atoms; and Y represents a halogen atom.

Namely, an amino ester represented by the formula (V) is reacted with an amine represented by the formula (VI) to thereby give an amidoamine represented by the formula (IV). Then, the amidoamine (IV) is reacted with a compound represented by the formula (VII), optionally followed by counter ion exchange reaction. Thus, the quaternary ammonium salt (II) can be prepared.

Examples of the amino ester (V) to be used in the above step include methyl N,N-dimethylaminoacetate, nethyl N-(2-hydroxyethyl)-N-methylaminoacetate, methyl N,N-bis(2-hydroxyethyl)aminoacetate, methyl N,N-dimethylaminopropionate, methyl N-(2-hydroxyethyl)-N-methylaminopropionate, methyl N,N-bis(2-hydroxyethyl)aminopropionate, methyl N,N-dimethylaminobutyrate, methyl N-(2-hydroxyethyl)-N-methylaminobutyrate, methyl N,N-bis(2-hydroxyethyl)aminobutyrate, methyl N,N-dimethylaminocaproate, methyl N-(2-hydroxyethyl)-N-methlaminocaproate and methyl N,N-bis(2-hydroxyethyl)aminocaproate, and ethyl esters and propyl esters of various aminocarboxylic acids.

Examples of the primary amine (VI) include octylamine, decylamine, dodecylamine, tetradecylamine, hexadecylamine, octadecylamine, cicosylamine, docosylamine, 2-ethylhexylamine, 2-butyloctylamine, 2-hexyldecylamine, 2-octyldodecylamine, 2-decyltetradecylamine, 2-dodecylhexadecylamine, 2-tetradecyloctadecylamine, 2-hexadecyleicosylamine, oleylamine, elaidylamine, and primary amines having alkyl groups which originate from natural fats and oils such as coconut oil, palm oil, beef tallow, rapeseed oil and fish oil. The primary amine (VI) is used either alone or in admixture of two or more.

The reaction between the amino ester (V) and the primary amine (VI) is effected in the presence or absence of a solvent such as ethanol, isopropanol and toluene and in the presence or absence of a catalyst such as sodium hydroxide, potassium hydroxide and sodium methylate. The molar ratio of the primary amine (VI) to the amino ester (V) ranges preferably from 0.8 to 1.5, still more preferably from 0.8 to 1.2, and the reaction temperature preferably ranges from 60° to 150° C.

The amidoamine (IV) thus obtained is then reacted with the compound (VII). As described in, for example, European Patent Publication-A No. 21,431 (published on Jan. 7, 1981), the compound (VII) can be prepared by reacting a halocarboxylic acid or a halocarboxylic acid chloride corresponding thereto with an alcohol or an alkylene oxide adduct thereof. Examples of the halocarboxylic acid include chloroacetic acid, chloroproplonic acid, chlorobutyric acid and chlorocaproic acid, while examples of the alcohol include octanol, decanol, dodecanol, tetradecanol, hexadecanol, octadecanol, eicosanol, docosanol, 2-ethylhexanol, 2-butyloctanol, 2-hexyldecanol, 2-octyldodecanol, 2-decyltetradecanol, 2-dodecylhexadecanol, 2-tetradecyloctadecanol, 2-hexadecyleicosanol, oleyl alcohol, elaidyl alcohol, and higher alcohols having an alkyl composition originating from natural fats and oils (for example, palm oil, beef tallow, rapeseed oil and fish oil). The halocarboxylic acid and the alcohol are each used alone or in admixtures of two or more halocarboxylic acids or two or more alcohols. Further, examples of the alkylene oxide adducts of these alcohols include ethylene oxide adducts of these alcohols, propylene oxide adducts of these alcohols, ethylene oxide/ propylene oxide random adducts of these alcohols, and ethylene oxide/ propylene oxide block adducts of these alcohols.

The reaction between the amidoamine (IV) with the compound (VII) is effected in the presence of a solvent such as ethanol, isopropanol and acetone at a temperature of from 40° to 130° C. The molar ratio of the compound (VII) to the amidoamine (IV) ranges preferably from 0.8 to 1.5, still more preferably from 0.8 to 1.2. The counter ion of the quaternary ammonium salt (II) thus obtained may be exchanged by using, for example, an ion exchange resin, if necessary. Needless to say, the quaternary ammonium salts obtained by effecting the counter ion exchange are also quaternary ammonium salts (II) according to the present invention. Such a quaternary ammonium salt (II) is a novel compound and its structure can be confirmed by its infrared absorption spectrum or nuclear magnetic resonance spectrum.

[Aqueous fabric softener composition]

The aqueous fabric softener composition of the present invention comprises from 3 to 40% by weight, preferably from 5 to 30% by weight and still preferably from 10 to 30% by weight, of the component (A), and water.

As component (A), the quaternary ammonium salt (I) and/or the quaternary ammonium salt (II) are used. When these salts are used together, the weight ratio of the quaternary ammonium salt (I) to the quaternary ammonium salt (II) [(I)/(II)] falls within a range of from 100/0 to 0/100.

When the amount of component (A) is smaller than 3% by weight, the concentration of the base in the softener composition is excessively low and thus no softening effect can be exerted on clothes. When the amount thereof exceeds 40% by weight, the composition becomes extremely viscous and thus suffers from some troubles, such that it is difficult to pour from a bottle.

To improve the softening performance and storage stability, the softener composition of the present invention may further comprise a linear or branched, saturated or unsaturated fatty acid(s) having 8 to 36 carbon atoms [component (B)]. The amount of component (B) in the composition of the present invention is not more than 100% by weight, preferably from 0.5 to 50% by weight, based on the weight of component (A).

Examples of the fatty acid as component (B) to be used herein include octadecanoic acid, hexadecanoic acid, tetradecanolc acid, dodecanoic acid, decanoic acid, octanoic acid, oleic acid, isostearic acid and fatty acids having an alkyl composition originating from natural fats and oils such as coconut oil, palm oil, beef tallow, rapeseed oil and fish oil.

To regulate the viscosity of the composition and to improve the storage stability of the composition (i.e., to prevent gelation), the composition of the present invention may furthermore contain a monohydric alcohol(s) having 1 to 4 carbon atoms [component (C)]. The amount of component (C) in the composition of the present invention is not more than 60% by weight, preferably from 5 to 50% by weight and still more preferably from 10 to 45% by weight, based on the weight of component (A).

Examples of the monohydric alcohol having 1 to 4 carbon atoms include methanol, ethanol, n-propanol, i-propanol, n-butanol, i-butanol, sec. butanol and tert. butanol.

In the composition of the present invention, a cationic compound (for example, a quaternary ammonium salt and an imidazolinium salt) which has been known as a softener base, an ester, an amide or a long-chain alcohol, or a mixture of two or more thereof may be incorporated therein. Examples of these compounds include quaternary ammonium salts represented by the following formula (III) [component (D)] and compounds represented by the following formulae (XVII-1) to (XVII-9) [component (G)].

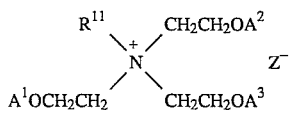 (III)

In the above formula, $R^{11}$ represents an alkyl or hydroxyalkyl group having 1 to 4 carbon atoms; $A^1$, $A^2$ and $A^3$ may be either the same or different from one another and each represents a hydrogen atom or a group represented by the formula: $R^{12}CO$— (wherein $R^{12}$ represents a linear or branched alkyl or alkenyl group having 7 to 35 carbon atoms) and at least one of $A^1$, $A^2$ and $A^3$ is a group represented by the following formula: $R^{12}CO$— (wherein $R^{12}$ represents as defined above), and $Z^-$ represents an anion group.

Examples of $Z^-$ include a halide ion such as $Cl^-$ and $Br^-$, and an alkyl ($C_1$ to $C_3$) sulfate group.

In the composition of the present invention, $Z^-$ in the quaternary ammonium salt represented by the formula (III) may be either the same as $X^-$ in the quaternary ammonium salts (I) or (II) which is simultaneously used, or different therefrom.

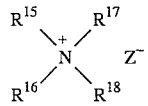 (XVII-1)

In the above formula, $R^{15}$ and $R^{16}$ may be either the same or different from each other and each represents a linear or branched alkyl, alkenyl or 2-hydroxyalkyl group having 10 to 24 carbon atoms; $R^{17}$ represents an alkyl or hydroxyalkyl group having 1 to 3 carbon atoms, a benzyl group or a group represented by —$(C_2H_4O)_mH$ (wherein m represents a number of from 1 to 3); $R^{18}$ represents a hydrogen atom, an alkyl or hydroxyalkyl group having 1 to 3 carbon atoms, a benzyl group or a group represented by —$(C_2H_4O)_mH$ (wherein m is as defined above); and $Z^-$ is as defined above.

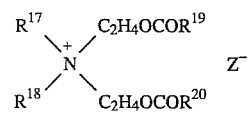 (XVII-2)

In the above formula, $R^{17}$ $R^{18}$ and $Z^-$ are each as defined above; and $R^{19}$ and $R^{20}$ may be either the same or different from each other and each represents a linear or branched alkyl, alkenyl or 2-hydroxyalkyl group having 9 to 23 carbon atoms.

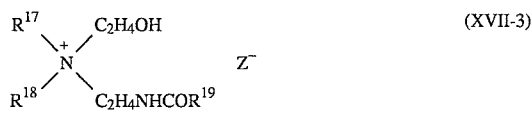 (XVII-3)

In the above formula, $R^{17}$, $R^{18}$, $R^{19}$ and $Z^-$ are each as defined above.

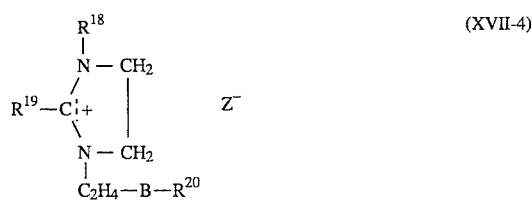 (XVII-4)

In the above formula, $R^{18}$, $R^{19}$, $R^{20}$ and $Z^-$ are each as defined above; and B represents a group represented by the formula: —OCO— or the formula: —NHCO—.

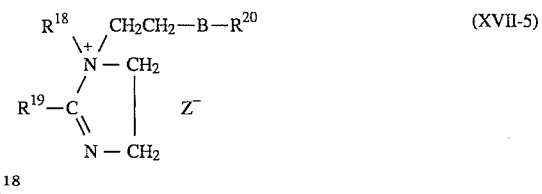 (XVII-5)

In the above formula, $R^{18}$, $R^{19}$, $R^{20}$, B and $Z^-$ are each as defined above.

 (XVII-6)

In the above formula, $R^{19}$ is as defined above.

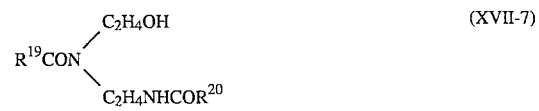 (XVII-7)

In the above formula, $R^{19}$ and $R^{20}$ are each as defined above.

 (XVII-8)

In the above formula, $R^{19}$ and $R^{20}$ are each as defined above; and $R^{21}$ represents a linear or branched alkyl, alkenyl or 2-hydroxyalkyl group having 9 to 23 carbon atoms.

 (XVII-9)

In the above formula, $R^{22}$ represents a linear or branched alkyl or alkenyl group having 10 to 24 carbon atoms.

Among these known cationic compounds, esters, amides and long-chain alcohols, a quaternary ammonium salt represented by the formula (III) [hereinafter referred to simply as the quaternary ammonium salt (III)] is preferably as a component to be incorporated into the composition according to the present invention. Namely, a combination of component (A) with a quaternary ammonium salt (III) may be cited as a preferable embodiment of the softener composition of the present invention.

Specific examples of the quaternary ammonium salt (III) are as follows.

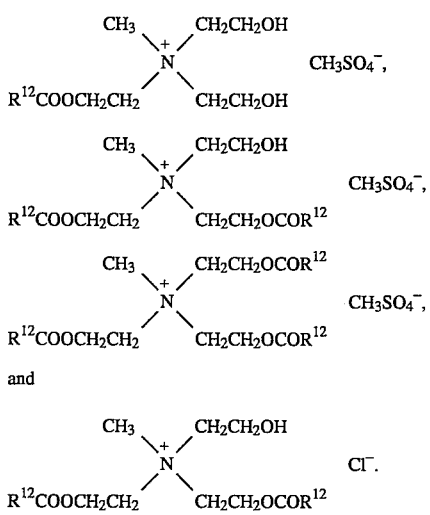

and $$\begin{array}{c} CH_3 \\ \diagdown \!\!\!{\overset{+}{\phantom{N}}}\!\!\!\diagup \ CH_2CH_2OH \\ N \\ \diagup \phantom{N} \diagdown \\ R^{12}COOCH_2CH_2 \phantom{xx} CH_2CH_2OCOR^{12} \end{array} \quad Cl^-.$$

In the above formulae, $R^{12}$ is as defined above.

The quaternary ammonium salt (III) [component (D)] can be incorporated in an amount of not more than 40% by weight, preferably from 3 to 30% by weight, based on the total weight of the composition. The total amount of components (A) and (D) is from 3 to 50% by weight, preferably from 5 to 40% by weight, based on the total weight of the composition. When the amount of the quaternary ammonium salt (III) exceeds 40% by weight based on the total weight of the composition in this case, the softener composition becomes extremely viscous and thus suffers from some troubles, such that it is difficult to pour from a bottle. When the total amount of components (A) and (D) is less than 3% by weight, the excessively low concentration of the softener base in the softener composition makes it impossible to exert a satisfactory softening effect on clothes. When the total amount of components (A) and (D) exceeds 50% by weight, on the other hand, the softener composition becomes extremely viscous and thus suffers from some troubles, such that it is difficult to pour from a bottle. Component (G) is used in an amount of not more than 50% by weight, preferably not more than 25% by weight, based on the weight of component (A).

When the concentration of component (A) or the total concentration of components (A) and (D) in the softener composition of the present invention is high, for example, more than 40% by weight based on the total weight of the composition, the composition tends to thicken during storage. In order to suppress the tendency to thicken, it is preferable to incorporate a polyether compound having a weight average molecular weight of from 5,000 to 2,000,000 which is obtained by adding ethylene oxide and, if necessary, propylene oxide and/or trimethylene oxide to a compound having at least 3 active hydrogen atoms, wherein the ratio of the oxyethylene groups is 55% by weight or more based on the molecular weight of the polyether compound, or a derivative thereof [component (E)], into the composition according to the present invention.

Examples of the compound having at least 3 active hydrogen atoms, which is used as a starting material for the preparation of component (E), are as follows.

Namely, polyhydric alcohols such as trimethylolpropane, diethanolamine, triethanolamine, glycerol, pentaerythritol, sorbitol, sucrose, polyglycerol, polyvinyl alcohol and partial saponification products of polyvinyl acetate; polyhydric phenols such as phenol resins and formalin condensates of alkylphenols; and polyamine compounds such as polyethyleneimines, for example, ethylenediamlne, diethylenetriamine, triethylenetetramine, tetraethylenepentamine and pentaethylenehexamine may be cited therefore. In addition, partial amidation products and N-alkylation products which are derivatives of these polyamine compounds may also be used therefore, so long as they have at least 3 active hydrogen atoms remaining therein.

Component (E) can be prepared by adding ethylene oxide, and, if necessary, propylene oxide and/or trimethylene oxide to a compound having at least 3 active hydrogen atoms by any conventional method. In particular, an adduct of ethylene oxide alone, a block adduct of ethylene oxide with propylene oxide and a partial block adduct of ethylene oxide with propylene oxide are preferable as component (E). When two or more alkylene oxides are added to the compound having at least 3 active hydrogen atoms, the order is arbitrary. However, the one which is obtained by adding propylene oxide (hereinafter referred to simply as PO), followed by the addition of ethylene oxide (hereinafter referred to simply as EO) is preferable from the viewpoint of suppression of the thickening of the composition during storage, when the concentration of component (A) or the total concentration of components (A) and (D) is high.

The weight-average molecular weight of component (E) ranges from 5,000 to 2,000,000, preferably from 10,000 to 100,000. The content of the oxyethylene (EO) chain moieties in the molecule is 55% by weight or more, preferably 80% by weight or more, based on the whole molecular weight.

When the molecular weight of component (E) is less than 5,000, only a limited effect of suppressing the thickening of the softener composition during storage can be achieved. When it exceeds 2,000,000, on the other hand, the softener composition becomes extremely viscous and thus suffers from some troubles, such that it is difficult to pour from a bottle.

When the ratio (total weight) of oxyethylene groups in the molecular weight of component (E) is less than 55% by weight, only a limited effect of suppressing the thickening of the softener composition during storage can be achieved.

Examples of the derivative of the polyether compound to be used as the component (E) include crosslinked products prepared by reacting the above-mentioned polyether compound with, for example, a compound having an isocyanate group, compounds prepared by sulfating, phosphorylating, carboxyalkylating or fatty acid-esterifying the terminal hydroxyl groups of polyether compounds and those prepared by partly cationizing nitrogen atoms of the same. Among these derivatives, fatty acid-esterification products and cationized products are particularly preferable.

As the fatty acids to be used in the preparation of the fatty acid-esterification products, those having 7 to 23 carbon atoms are preferable, but neither the number of double bonds nor the presence or absence of branching exerts any considerable effect on the performance.

Examples of the cationized product include those prepared by partly cationizing nitrogen atoms of the polyether compound with a dialkylsulfate or an alkyl halide and those prepared by neutralizing a cationized compound with acetic acid or an alkylbenzenesulfonic acid.

The aqueous fabric softener composition of the present invention contains 0.5 to 5% by weight, preferably 1 to 3% by weight, based on the total weight of the composition, of component (E). The weight ratio of component (E) to component (A) [component (E)]/[component (A)] is from 1/100 to 1/2.5, preferably from 1/50 to 1/5. Further, the total amount of components (A) and (E) in the softener composition of the present invention is from 4 to 45% by weight, preferably from 11 to 39% by weight and still more preferably from 14 to 32% by weight, based on the total weight of the composition. When the amount of component (E) is in the above-mentioned ranges, the softener composition of the present invention exerts a softening performance at a level desired in the present invention and, at the same time, the tendency toward the thickening of the composition during storage is suppressed.

To further improve the softening performance and storage stability of the composition of the present invention, an amidoamine represented by the following formula (IV) or an acid salt thereof [component (F)] may be added thereto.

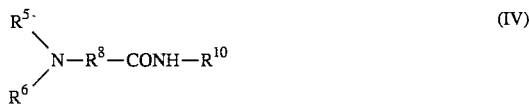

In the above formula, $R^5$, $R^6$, $R^8$ and $R^{10}$ are each as defined above.

Examples of the amidoamine represented by the formula (IV) and its acid salt are as follows:

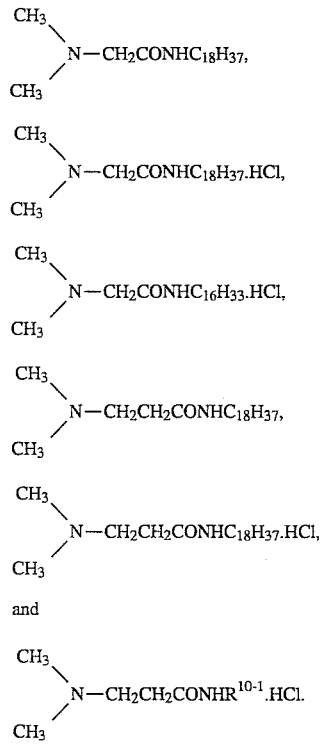

In the above formulas, $R^{10\text{-}1}$ represents an alkyl group obtained by substituting a methylene group for a carboxyl group of a hardened beef tallow fatty acid.

The amount of component (F) in the composition of the present invention is not more than 110% by weight, preferably from 1 to 100% by weight, based on the weight of component (A).

When component (A) of the present invention is the quaternary ammonium salt (I), a quaternary ammonium salt represented by the following formula (XX) [hereinafter referred to simply as quaternary ammonium salt (XX)] [component (H)] may be incorporated into the composition of the present invention to further improve the softening performance and storage stability thereof.

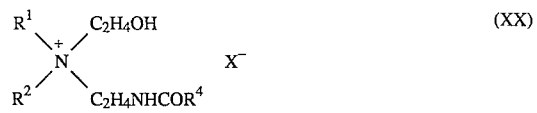

In the above formula, $R^1$, $R^2$, $R^4$ and $X^-$ are each as defined above.

The amount of component (H) in the composition of the present invention is not more than 110% by weight, preferably 1 to 100% by weight, based on the weight of the quaternary ammonium salt (I).

The $X^-$ group in the quaternary ammonium salt (XX) to be used in the present invention represents an anion group, and examples thereof include halide anion groups such as $Cl^-$ and $Br^-$ and alkyl ($C_1$ to $C_5$) sulfate groups such as $CH_3SO_4^-$, $C_2H_5SO_4^-$ and $C_3H_7SO_4^-$. Examples of the quaternary ammonium salt (XX) are as follows:

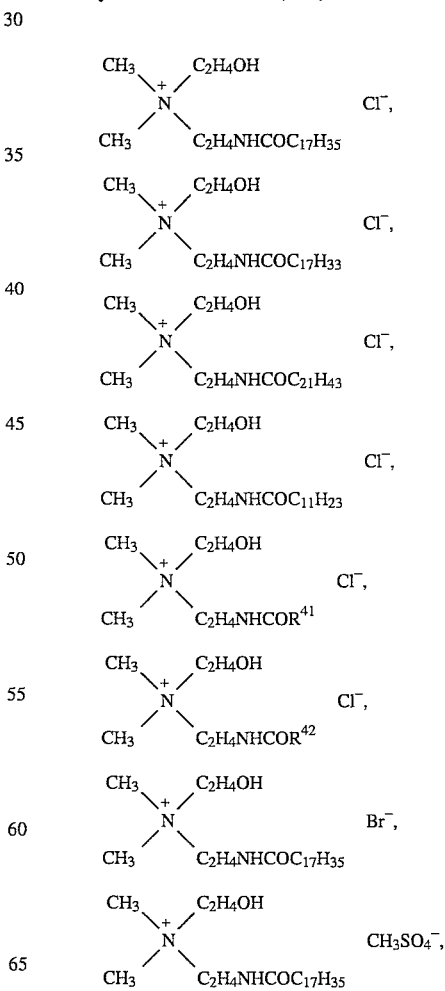

and

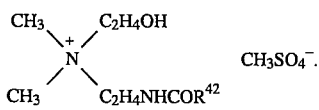

In the formulas cited above, $R^{41}$ represents an alkyl group obtained by eliminating a carboxyl group from hardened beef tallow fatty acid; and $R^{42}$ represents an alkyl group obtained by eliminating a carboxyl group from hardened palm oil fatty acid.

The quaternary ammonium salt (XX) may be prepared, for example, in accordance with the following scheme.

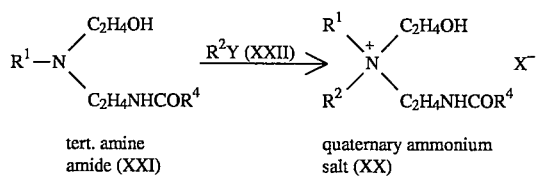

tert. amine amide (XXI)  quaternary ammonium salt (XX)

In the above formula, $R^1$, $R^2$, $R^4$, $X^-$ and Y are each as defined above.

Namely, the tert. amine amide (XXI) is quaternized by a known method with the use of a quaternizing agent (XXII) to thereby give a quaternary ammonium salt (XX). If necessary, the counter ion of the quaternary ammonium salt (XX) thus obtained may be exchanged. Examples of the quaternizing agent (XXII) include alkyl halides (for example, methyl chloride, ethyl chloride and methyl bromide) and dialkylsulfates (for example, dimetylsulfate and diethylsulfate).

When component (A) of the present invention is the quaternary ammonium salt (II), a quaternary ammonium salt represented by the following formula (XXII) or a long-chain fatty acid represented by the following formula (XXIV) may be incorporated into the composition of the present invention:

wherein $R^{16}$, $R^{17}$ and $R^{18}$ are each as defined above; and p and q are the same or different from each other and each represents a number of 1 to 5, and $R^{19}COOH$ (XXIV)

wherein $R^{19}$ is as defined above.

When component (A) of the present invention is the quaternary ammonium salt (I) or (II), a quaternary ammonium salt represented by the following formula (XXV) may be incorporated into the composition of the present invention:

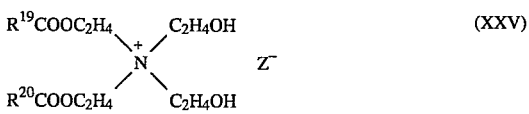

wherein $R^{19}$, $R^{20}$ and $Z^-$ are each as defined above.

The composition of the present invention may contain an inorganic electrolyte such as NaCl, $CaCl_2$ and $MgCl_2$ to thereby regulate the viscosity of the composition. In such a case, the amount of the inorganic electrolyte ranges from 0 to 2% by weight, preferably from 0.01 to 1% by weight, based on the total weight of the composition.

The softener composition of the present invention may further contain an acidic or alkaline substance to thereby regulate the pit value of the composition. In such a case, the acidic or alkaline substance is added to thereby regulate the pH value of the composition in a range of preferably from 1.5 to 6.5, still more preferably from 2.0 to 6.0, from the viewpoint of the viscosity and storage stability of the composition.

Although the softener composition of the present invention remains stable over prolonged storage, its stability under more sever conditions may be elevated by further adding a nonionic surfactant such as polyoxyethylene (5 to 50 mol) alkyl or alkenyl ($C_{12}$ to $C_{14}$) ethers and polyoxyethylene (5 to 50 mol) alkyl or alkenyl ($C_{12}$ to $C_{14}$) amines or a hydrotrope such as ethylene glycol, propylene glycol and urea thereto.

Furthermore, the composition of the present invention may contain a pigment or a dye to improve its appearance, silicone to suppress foaming in the rinsing step and a fragrance.

Now, an example of the process for the preparation of the softener composition of the present invention will be described, though the process for the preparation is not restricted thereto.

Component (A) or a mixture thereof with other component(s) [excepting component (E)] is molten. Then, the molten product is slowly dropped into deionized water which is maintained at 60° C. under stirring to prepare an emulsion. Then, if necessary, component (E) may be added to the emulsion thus Formed. Furthermore, an aqueous solution of a nonionic surfactant may be used in place of the deionized water, or an inorganic salt may be added after the addition of components (A) to (tI) to thereby regulate the viscosity of the composition.

The softener composition according to the present invention can impart a sufficient softness, antistatic characteristics and an excellent elasticity to various fibers, and is extremely excellent in storage stability (i.e., the composition does not gel or become extremely viscous during storage, and the softening base does not suffer from hydrolysis during storage).

Further, since the quaternary ammonium salts (I) and (II) which are used as softening bases in the softener composition of the present invention are excellent in biodegradability, the softener composition of the present invention is also nondetrimental to the natural environment.

EXAMPLES

The present invention will now be described in more detail with reference to the following Examples which should not be considered to limit the scope of the present invention.

First, Synthesis Examples of the quaternary ammonium salts (I) and (II) according to the present invention will be given.

Synthesis Example 1

[synthesis of quaternary ammonium salt (I-1)]

284 g of stearic acid and 134 g of N-(2-aminoethyl)ethanolamine were fed into a four-necked flask provided with a stirrer, a thermometer and a Liebig condenser and were heated to 200° C. Then, the pressure in the flask was reduced to 600 Torr, and the contents in the flask were allowed to react for 8 hours. Then, the pressure in the flask was further reduced to 5 Torr and the reaction mixture in the flask was stirred for 2 hours. After cooling, 150 ml of ethanol, 54 g of water and 1.2 g of sodium hydroxide were added to the reaction mixture in the flask. The mixture thus obtained was allowed to react at 80° C. for 2 hours. By recrystallizing the reaction product thus obtained from ethanol, 200 g of an amidoamine represented by the following structural formula (1) was obtained.

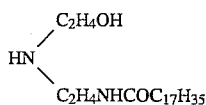

Next, 111 g of the above-mentioned amidoamine and 150 ml of isopropanol were fed into a four-necked flask provided with a stirrer, a thermometer and a condenser and were heated to 80° C. Then, 28 g of 35% formaldehyde and subsequently 15.5 g of formic acid were dropwise added to the mixture in the flask at the same temperature. Then, the contents in the flask. were allowed to react at 80° C. for 4 hours. The reaction product thus obtained was washed with 100-ml portions of water thrice, and then recrystallized from acetone. Thus, 80 g of a methylated compound represented by the following structural formula (2) was obtained.

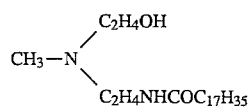

Next, 77 g of the above-mentioned methylated compound and 60 g of stearic acid were fed into a four-necked flask provided with a stirrer, a thermometer and a dehydrating tube and allowed to react at 180° C. for 10 hours. Thus, a compound represented by the following structural formula (3) was obtained.

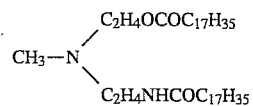

75 g of this compound and 21 g of isopropanol were fed into an autoclave and 7 g of chloromethane was injected thereinto. Then, the contents in the autoclave were allowed to react at 90° C. for 8 hours. The reaction product thus obtained was recrystallized from acetone to thereby give 70 g of a quaternary ammonium salt (I-1) represented by the following structural formula.

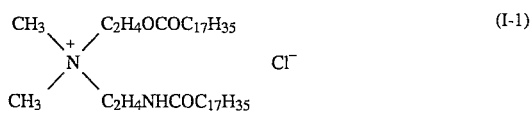

Synthesis Example 2

[synthesis of quaternary ammonium salt (I-2)]

The procedure of the above Synthesis Example 1 was repeated to thereby give a compound represented by the following structural formula (4).

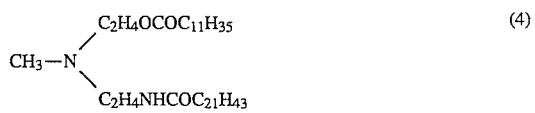

62 g of this compound (4) and 15 g of isopropanol were fed into a four-necked flask provided with a stirrer, a thermometer and a condenser, and were heated to 80° C. Thus, the compound (4) was dissolved in isopropanol. Then, 12 g of dimethylsulfate was dropwise added to the solution in the flask over one hour. The contents in the flask were allowed to react at 80° C. for 6 hours. The reaction product thus obtained was recrystallized from acetone to thereby give 65 g of a quaternary ammonium salt (I-2) represented by the following structural formula.

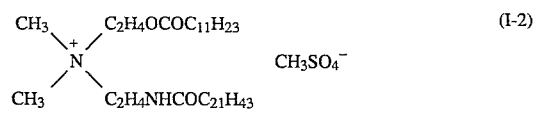

Synthesis Examples 3 to 6

[synthesis of quaternary ammonium salts (I-3) to (I-6)]

The procedure of the above Synthesis Example 1 was repeated to thereby give the quaternary ammonium salts (I-3) to (I-6) as will be listed in the following Table 1.

Synthesis Example 7

[synthesis of quaternary ammonium salt (II-1)]

179 g of octadecylamine and 86 g of methyl N,N-dimethylaminoacetate were fed into a four-necked flask provided with a stirrer, a thermometer and a condenser and heated to 110° C. Then, the contents in the flask was allowed to react at the same temperature for 20 hours. After recrystallizing the reaction product thus obtained from acetone, 200 g of an amidoamine was obtained.

Subsequently, 57 g of the above-mentioned amidoamine, 400 ml of acetone and 60 g of octadecyl chloroacetate were fed into a four-necked flask provided with a stirrer, a thermometer and a condenser and allowed to react at 55° C. for 10 hours. The crystals thus precipitated were collected by filtration and dried to thereby give 80 g of the target compound.

It was confirmed by NMR spectrum and IR spectrum that this compound had the following structure.

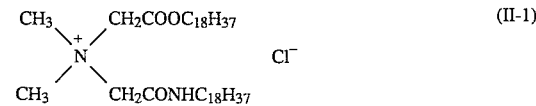

NMR spectrum (CDCl₃, internal standard: TMS)

3.3 ppm (q, 2H) $-\overset{O}{\overset{\|}{C}}NH-C\underline{H_2}-$, 3.6 ppm (s, 6H) $C\underline{H_3}-\overset{+}{N}-C\underline{H_3}$, 4.2 ppm (t, 2H) $-\overset{O}{\overset{\|}{C}}O-C\underline{H_2}-$, 4.7 ppm (s, 2H) $-\overset{+}{N}-C\underline{H_2}-\overset{O}{\overset{\|}{C}}O-$, 4.9 ppm (s, 2H) $-\overset{+}{N}-C\underline{H_2}-\overset{O}{\overset{\|}{C}}NH-$, and 9.2 ppm (1H) $-\overset{O}{\overset{\|}{C}}N\underline{H}-$.

IR spectrum (KBr tablet) 1761 cm⁻¹, 1677 cm⁻¹ and 1578 cm⁻¹.

Synthesis Example 8

[synthesis of quaternary ammonium salt (II-2)]

150 g of octadecylamine and 90 g of ethyl N,N-dimethylaminopropionate were fed into a four-necked flask provided with a stirrer, a thermometer and a condenser. After adding 5.9 g of sodium methylate (a 28% solution in methanol), the contents in the flask were heated to 105° C. and then allowed to react at the same temperature for 5 hours. After recrystallizing the reaction product thus obtained from acetone, 145 g of an amidoamine was obtained.

Subsequently, 30 g of the above-mentioned amidoamine, 300 ml of acetone and 27 g of octadecyl chloroacetate were fed into a four-necked flask provided with a stirrer, a thermometer and a condenser and allowed to react at 55° C. for 25 hours. The crystals thus precipitated were collected by filtration and dried to thereby give 40 g of the target compound.

Based on the NMR spectrum and IR spectrum, it was confirmed that this compound had the following structure.

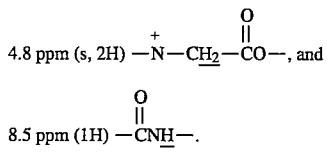  (II-2)

NMR spectrum (CDCl₃, internal standard: TMS)

3.1 ppm (t, 2H) $-C\underline{H_2}-\overset{O}{\overset{\|}{C}}NH-$, 3.2 ppm (q, 2H) $-\overset{O}{\overset{\|}{C}}NH-C\underline{H_2}-$, 3.5 ppm (s, 6H) $C\underline{H_3}-\overset{+}{N}-C\underline{H_3}$, 4.1 ppm (t, 2H) $-\overset{+}{N}-C\underline{H_2}C\underline{H_2}\overset{O}{\overset{\|}{C}}NH-$, 4.2 ppm (t, 2H) $-\overset{O}{\overset{\|}{C}}O-C\underline{H_2}-$, 4.8 ppm (s, 2H) $-\overset{+}{N}-C\underline{H_2}-\overset{O}{\overset{\|}{C}}O-$, and 8.5 ppm (1H) $-\overset{O}{\overset{\|}{C}}N\underline{H}-$.

IR spectrum (KBr tablet) 1758 cm⁻¹, 1680 cm⁻¹, and 1542 cm⁻¹.

Synthesis Example 9

[synthesis of quaternary ammonium salt (II-3)]

A quaternary ammonium salt (II-3) was obtained by the same procedure as the one of Synthesis Example 7. Based on the NMR spectrum, it was confirmed that the compound obtained had the following structure.

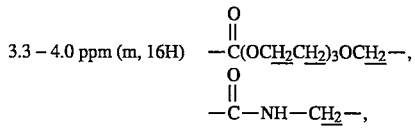  (II-3)

NMR spectrum (CDCl₃, internal standard: TMS)

3.3 – 4.0 ppm (m, 16H)  $-\overset{O}{\overset{\|}{C}}(OC\underline{H_2}C\underline{H_2})_3OC\underline{H_2}-$,
$-\overset{O}{\overset{\|}{C}}-NH-C\underline{H_2}-$, 3.6 ppm (s, 6H)  $C\underline{H_3}-\overset{+}{N}-C\underline{H_3}$ 4.7 ppm (s, 2H)  $\overset{+}{N}-C\underline{H_2}-\overset{O}{\overset{\|}{C}}O-$, and 4.9 ppm (s, 2H)  $-\overset{+}{N}-C\underline{H_2}-\overset{O}{\overset{\|}{C}}-NH-$.

Synthesis Example 10

(Synthesis of quaternary ammonium salt (II-4)]

A quaternary ammonium salt (II-4) was obtained by the same procedure as the one of Synthesis Example 7. Based on the NMR spectrum, it was confirmed that the compound obtained had the following structure.

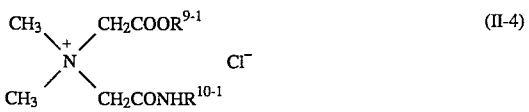  (II-4)

wherein R⁹⁻¹ and R¹⁰⁻¹ represent each an alkyl group obtained by substituting a methylene group for a carboxyl group of hardened beef tallow fatty acid.

NMR spectrum (CDCl₃, internal standard: TMS)

3.3 ppm (q, 2H)  $-\overset{O}{\overset{\|}{C}}NH-C\underline{H_2}-$, 3.6 ppm (s, 6H)  $C\underline{H_3}-\overset{+}{N}-C\underline{H_3}$, 4.2 ppm (t, 2H)  $-\underset{\|}{\overset{O}{C}}-C\underline{H}_2-$, 4.7 ppm (s, 2H)  $-\overset{+}{N}-C\underline{H}_2-\underset{\|}{\overset{O}{C}}O-$, 4.9 ppm (s, 2H)  $-\overset{+}{N}-C\underline{H}_2-\underset{\|}{\overset{O}{C}}NH-$, and 9.2 ppm (1H)  $-\underset{\|}{\overset{O}{C}}N\underline{H}-$.

Synthesis Example 11

[synthesis of quaternary ammonium salt (II-5)]

A quaternary ammonium salt (II-5) was obtained by he same procedure as the one of Synthesis Example 7. Based on the NMR spectrum, it was confirmed that the compound obtained had the following structure.

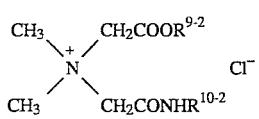

wherein $R^{9-2}$ and $R^{10-2}$ represent each an alkyl group obtained by substituting a methylene group for a carboxyl group of hardened palm oil fatty acid.

NMR spectrum (CDCl$_3$, internal standard: TMS)

3.3 ppm (q, 2H)  $-\underset{\|}{\overset{O}{C}}NH-C\underline{H}_2-$, 3.6 ppm (s, 6H)  $C\underline{H}_3-\overset{+}{N}-C\underline{H}_3$, 4.2 ppm (t, 2H)  $-\underset{\|}{\overset{O}{C}}-C\underline{H}_2-$, 4.7 ppm (s, 2H)  $-\overset{+}{N}-C\underline{H}_2-\underset{\|}{\overset{O}{C}}O-$, 4.9 ppm (s, 2H)  $-\overset{+}{N}-C\underline{H}_2-\underset{\|}{\overset{O}{C}}NH-$, and 9.2 ppm (1H)  $-\underset{\|}{\overset{O}{C}}N\underline{H}-$.

Synthesis Example 12

[Synthesis of quaternary ammonium salt (II-6)]

A quaternary ammonium salt (II-6) was obtained by the same procedure as the one of Synthesis Example 7. Based on the NMR spectrum, it was confirmed that the compound obtained had the following structure.

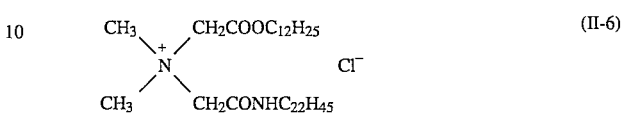

NMR spectrum (CDCl$_3$, internal standard: TMS)

3.3 ppm (q, 2H)  $-\underset{\|}{\overset{O}{C}}NH-C\underline{H}_2-$, 3.6 ppm (s, 6H)  $C\underline{H}_3-\overset{+}{N}-C\underline{H}_3$, 4.2 ppm (t, 2H)  $-\underset{\|}{\overset{O}{C}}-C\underline{H}_2-$, 4.7 ppm (s, 2H)  $-\overset{+}{N}-C\underline{H}_2-\underset{\|}{\overset{O}{C}}O-$, 4.9 ppm (S, 2H)  $-\overset{+}{N}-C\underline{H}_2-\underset{\|}{\overset{O}{C}}NH-$, and 9.2 ppm (1H)  $-\underset{\|}{\overset{O}{C}}N\underline{H}-$.

Synthesis Example 13

[synthesis of quaternary ammonium salt (II-7)]

A quaternary ammonium salt (II-7) was obtained by the same procedure as the one of Synthesis Example 8. Based on the NMR spectrum, it was confirmed that the compound obtained had the following structure.

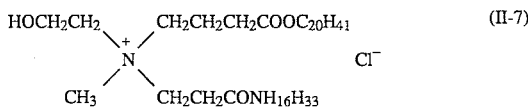

NMR spectrum (CDCl$_3$, internal standard: TMS)

1.8 ppm (m, 2H)  $\overset{+}{N}-CH_2C\underline{H}_2CH_2CO-$, 2.4 ppm (t, 2H)  $-C\underline{H}_2COO-$, 3.1 ppm (t, 2H)  $-C\underline{H}_2CONH-$, 3.3 ppm (t, 2H)  $-CONHC\underline{H}_2-$, 3.4 ppm (s, 3H)  $C\underline{H}_3-\overset{+}{N}-$, 3.5 ppm (4H)  $HOCH_2C\underline{H}_2-\overset{+}{N}-C\underline{H}_2CH_2CH_2COO-$, 3.8 ppm (t, 2H)  $HOC\underline{H}_2CH_2-$, -continued 4.1 ppm (t, 2H)  $\overset{+}{N}-C\underline{H_2}CH_2CONH-$, and 4.2 ppm (t, 2H)  $-\overset{O}{\overset{\|}{C}}O-C\underline{H_2}-$.

Synthesis Example 14

[synthesis of quaternary ammonium salt (II-8)]

A quaternary ammonium salt (II-8) was obtained by the same procedure as the one of Synthesis Example 7. Based on the NMR spectrum, it was confirmed that the compound obtained had the following structure.

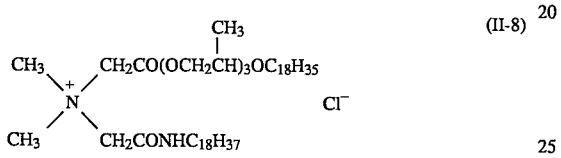  (II-8)

5NMR spectrum (CDCl$_3$, internal standard: TMS)

1.2 ppm (m, 9H)  $-(OC\underline{H_2}C\underline{H})_3-$, 3.3 ppm (t, 2H)  $-\overset{O}{\overset{\|}{C}}NH-C\underline{H_2}-$, 3.5–3.6 ppm (m, 9H)  $\overset{O}{\overset{\|}{C}}-OC\underline{H_2}C\underline{H}-(OC\underline{H_2}C\underline{H})_2-OC\underline{H_2}-$, 3.6 ppm (s, 6H)  $C\underline{H_3}-\overset{+}{N}-C\underline{H_3}$, 4.0 ppm (d, 2H)  $\overset{O}{\overset{\|}{C}}-OC\underline{H_2}-$, 4.7 ppm (s, 2H)  $\overset{+}{N}-C\underline{H_2}-\overset{O}{\overset{\|}{C}}O-$, and 4.9 ppm (s, 2H)  $\overset{+}{N}-C\underline{H_2}-CONH-$.

Synthesis Example 15

[synthesis of quaternary ammonium salt (II-9)]

A quaternary ammonium salt (II-9) was obtained by the same procedure as the one of Synthesis Example 8. Based on the NMR spectrum, it was confirmed that the compound obtained had the following structure.

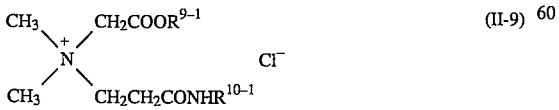  (II-9)

wherein $R^{9-1}$ and $R^{10-1}$ represent each an alkyl group obtained by substituting a methylene group for a carboxyl group of hardened beef tallow fatty acid.

NMR spectrum (CDCl$_3$, internal standard: TMS)

3.1 ppm (t, 2H)  $-C\underline{H_2}-\overset{O}{\overset{\|}{C}}NH-$, 3.2 ppm (q, 2H)  $-\overset{O}{\overset{\|}{C}}NH-C\underline{H_2}-$, 3.5 ppm (s, 6H)  $C\underline{H_3}-\overset{+}{N}-C\underline{H_3}$, 4.1 ppm (t, 2H)  $-\overset{+}{N}-C\underline{H_2}CH_2\overset{O}{\overset{\|}{C}}NH-$, 4.2 ppm (t, 2H)  $-\overset{O}{\overset{\|}{C}}O-C\underline{H_2}-$, 4.8 ppm (s, 2H)  $-\overset{+}{N}-C\underline{H_2}-\overset{O}{\overset{\|}{C}}O-$, and 8.5 ppm (1H)  $-\overset{O}{\overset{\|}{C}}N\underline{H}-$.

Synthesis Example 16

[synthesis of quaternary ammonium salt (II-10)]

A quaternary ammonium salt (II-10) was obtained by the same procedure as the one of Synthesis Example 8. Based on the NMR spectrum, it was confirmed that the compound obtained had the following structure.

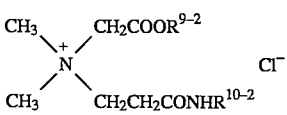  (II-10)

wherein $R^{9-2}$ and $R^{10-2}$ represent each an alkyl group obtained by substituting a methylene group for a carboxyl group of hardened palm oil fatty acid.

NMR spectrum (CDCl$_3$, internal standard: TMS)

3.1 ppm (t, 2H)  $-C\underline{H_2}-\overset{O}{\overset{\|}{C}}NH-$, 3.2 ppm (q, 2H)  $-\overset{O}{\overset{\|}{C}}NH-C\underline{H_2}-$, 3.5 ppm (s, 6H)  $C\underline{H_3}-\overset{+}{N}-C\underline{H_3}$, 4.1 ppm (t, 2H)  $-\overset{+}{N}-C\underline{H_2}CH_2\overset{O}{\overset{\|}{C}}NH-$, 4.2 ppm (t, 2H)  $-\overset{O}{\overset{\|}{C}}O-C\underline{H_2}-$, 4.8 ppm (s, 2H)  $-\overset{+}{N}-C\underline{H_2}-\overset{O}{\overset{\|}{C}}O-$, and 8.5 ppm (1H)  $-\overset{O}{\overset{\|}{C}}N\underline{H}-$.

Synthesis Example 17

[synthesis of quaternary ammonium salt (II-11)]

30 g of the amidoamine obtained in Synthesis Example 8, 80 ml of isopropanol and 27 g of oleyl chloroacetate were fed into a four-necked flask provided with a stirrer, a thermometer and a condenser and allowed to react at 75° C. for 15 hours. The reaction mixture thus obtained was distilled off under reduced pressure to remove the solvent. Thus, 55 g of the target compound was obtained.

Based on the NMR spectrum and IR spectrum, it was confirmed that the compound obtained had the following structure.

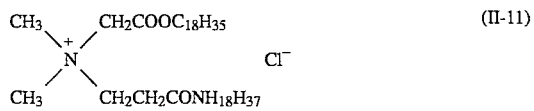

(II-11)

NMR spectrum (CDCl$_3$, internal standard: TMS)

| | | |
|---|---|---|
| 3.1 ppm (t, 2H) | $-CH_2-\overset{O}{\overset{\|}{C}}NH-$, | |
| 3.2 ppm (q, 2H) | $-\overset{O}{\overset{\|}{C}}NH-CH_2-$, | |
| 3.5 ppm (s, 6H) | $C\underline{H_3}-\overset{+}{N}-C\underline{H_3}$, | |
| 4.1 ppm (t, 2H) | $-\overset{+}{N}-C\underline{H_2}CH_2\overset{O}{\overset{\|}{C}}NH-$, | |
| 4.2 ppm (t, 2H) | $-\overset{O}{\overset{\|}{C}}O-C\underline{H_2}-$, | |
| 4.8 ppm (s, 2H) | $-\overset{+}{N}-C\underline{H_2}-\overset{O}{\overset{\|}{C}}O-$, | |
| 5.3 ppm (2H) | $-C\underline{H}=CH-$, and | |
| 8.5 ppm (1H) | $-\overset{O}{\overset{\|}{C}}N\underline{H}-$. | |

IR spectrum (KBr tablet). 1758 cm$^{-1}$, 1680 cm$^{-1}$, and 1542 cm$^{-1}$.

Synthesis Example 18

[synthesis of quaternary ammonium salt (II-12)]

120 g of docosylamine and 65 g of methyl N,N-dimethylaminocaproate were fed into a four-necked flask provided with a stirrer, a thermometer and a condenser, heated to 110° C. and then allowed to react at the same temperature for 20 hours. After recrystallizing the reaction product thus obtained from acetone, 110 g of an amidoamine was obtained.

Subsequently, 50 g of the above-mentioned amidoamine, 100 ml of isopropanol and 55 g of chlorobutyrate of an ethylene oxide adduct (3 mol on the average) of dodecyl alcohol were fed into a Four-necked flask provided with a stirrer, a thermometer and a condenser and allowed to react at 75° C. for 10 hours. The reaction mixture thus obtained was distilled off to remove the solvent. The reaction product thus obtained was recrystallized from acetone and dried to thereby give 80 g of the target compound.

Based on the NMR spectrum and IR spectrum, it was confirmed that the compound obtained had the following structure.

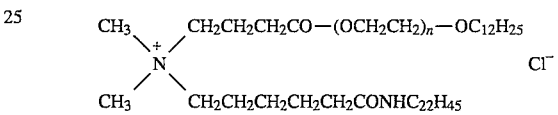

NMR spectrum (CDCl$_3$, internal standard: TMS)

| | |
|---|---|
| 2.1 ppm | $-C\underline{H_2}\overset{O}{\overset{\|}{C}}NH-$, $-C\underline{H_2}\overset{O}{\overset{\|}{C}}O-$, |
| 3.3–4.0 ppm | $-(OC\underline{H_2}CH_2)_n-OC\underline{H_2}-$, $-C\underline{H_2}-\overset{+}{N}-C\underline{H_2}-$, |
| 3.5 ppm (s, 6H) | $C\underline{H_3}-\overset{+}{N}-C\underline{H_3}$, and |
| 6.5 ppm (t, 1H) | $-\overset{O}{\overset{\|}{C}}N\underline{H}-$. |

IR spectrum (KBr tablet) 1760 cm$^{-1}$, 1679 cm$^{-1}$, and 1545 cm$^{-1}$.

The quaternary ammonium salts (I) and (II) [component (A)] obtained in the above-described Synthesis Examples 1 to 18 are summarized in the following Tables 1 and 2.

TABLE 1

| Synth. Ex. no. | Component (A) | | | | |
|---|---|---|---|---|---|
| 1 | 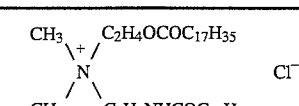 | (I-1) | 2 | 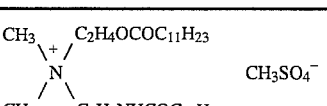 | (I-2) |
| 3 | 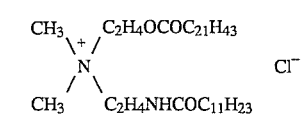 | (I-3) | 4 | 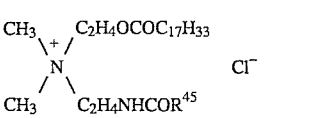 | (I-4)*¹ |

TABLE 1-continued

| Synth. Ex. no. | Component (A) | | | |
|---|---|---|---|---|
| 5 | CH₃\\N⁺/C₂H₄OCOR³⁻¹ / CH₃  C₂H₄NHCOR⁴⁻¹   Cl⁻ | (I-5)*² | 6 | CH₃\\N⁺/C₂H₄OCOR³⁻² / CH₃  C₂H₄NHCOR⁴⁻²   Cl⁻ | (I-6)*³ |
| 7 | CH₃\\N⁺/CH₂COOC₁₈H₃₇ / CH₃  CH₂CONHC₁₈H₃₇   Cl⁻ | (II-1) | 8 | CH₃\\N⁺/CH₂COOC₁₈H₃₇ / CH₃  CH₂CH₂CONHC₁₈H₃₇   Cl⁻ | (II-2) |
| 9 | CH₃\\N⁺/CH₂CO(OCH₂CH₂)₃OC₁₈H₃₇ / CH₃  CH₂CONHC₁₈H₃₇   Cl⁻ | (II-3) | 10 | CH₃\\N⁺/CH₂COOR⁹⁻¹ / CH₃  CH₂CONHR¹⁰⁻¹   Cl⁻ | (II-4)*⁴ |

TABLE 2

| Synth. Ex. no. | Component (A) | | | |
|---|---|---|---|---|
| 11 | CH₃\\N⁺/CH₂COOR⁹⁻² / CH₃  CH₂CONHR¹⁰⁻²   Cl⁻ | (II-5)*⁵ | 12 | CH₃\\N⁺/CH₂COOC₁₂H₂₅ / CH₃  CH₂CONHC₂₂H₄₅   Cl⁻ | (II-6) |
| 13 | HOCH₂CH₂\\N⁺/CH₂CH₂CH₂COOC₂₀H₄₁ / CH₃  CH₂CH₂CONHC₁₆H₃₃   Cl⁻ | (II-7) | 14 | CH₃ \| CH₃\\N⁺/CH₂CO(OCH₂CH)₃OC₁₈H₃₅ / CH₃  CH₂CONHC₁₈H₃₇   Cl⁻ | (II-8) |
| 15 | CH₃\\N⁺/CH₂COOR⁹⁻¹ / CH₃  CH₂CH₂CONHR¹⁰⁻¹   Cl⁻ | (II-9)*⁴ | 16 | CH₃\\N⁺/CH₂COOR⁹⁻² / CH₃  CH₂CH₂CONHR¹⁰⁻²   Cl⁻ | (II-10)*⁵ |
| 17 | CH₃\\N⁺/CH₂COOC₁₈H₃₅ / CH₃  CH₂CH₂CONHC₁₈H₃₇   Cl⁻ | (II-11) | 18 | CH₃\\N⁺/(CH₂)₃CO(OCH₂CH₂)ₙOC₁₂H₂₅ / CH₃  (CH₂)₅CONHC₂₂H₄₅   Cl⁻ (n = 3 (average)) | (II-12) |

Note)
*¹ $R^{45}$ represents an alkyl group obtained by eliminating a carboxyl group from oleic acid.
*² $R^{3-1}$ and $R^{4-1}$ represent each an alkyl group obtained by eliminating a carboxyl group from hardened beef tallow fatty acid.
*³ $R^{3-2}$ and $R^{4-2}$ represent each an alkyl group obtained by eliminating a carboxyl group from hardened palm oil fatty acid.
*⁴ $R^{9-1}$ and $R^{10-1}$ represent each an alkyl group obtained by substituting a methylene group for a carboxyl group of hardened beef tallow fatty acid.
*⁵ $R^{9-2}$ and $R^{10-2}$ represent each an alkyl group obtained by substituting a methylene group for a carboxyl group of hardened palm oil fatty acid.

Examples 1 to 49 and Comparative Examples 1 to 19

Softener compositions comprising component (A) as specified in Tables 1 and 2, component (D) as specified in Table 3, component (E) as specified in Table 4, component (F) as specified in Table 5, fatty acids [component (B)], lower alcohols [component (C)] and others each at a ratio as specified in Tables 6 to 11 were prepared (with the pit value being adjusted to 3). The balance was water. In Tables 6 to 11, each number in the brackets stands for the amount in the softener composition expressed in % by weight.

Each softener composition thus obtained was evaluated for softness, elasticity and storage stability by the methods described below. Tables 12 to 14 summarize the results.

In Comparative Examples, compounds (i) to (v) as given below were employed in place of component (A).

compound (i)

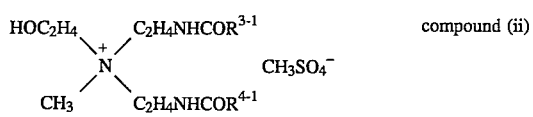

compound (ii)

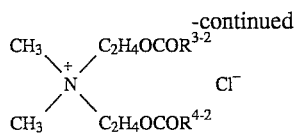

compound (iii)

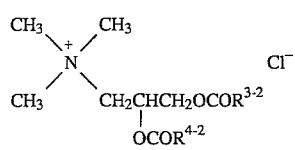

compound (iv)

and

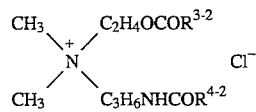

compound (v)

In the above formulae, $R^{3-1}$ and $R^{4-1}$ represent each an alkyl group obtained by eliminating a carboxyl group from hardened beef tallow fatty acid, $R^{3-2}$ and $R^{4-2}$ represent each an alkyl group obtained by eliminating a carboxyl group from hardened palm oil fatty acid, and $R^{3-3}$ and $R^{4-3}$ represent each an alkyl group obtained by substituting a methylene group for a carboxyl group of hardened beef tallow fatty acid.

TABLE 3

Component (D)

D-1*[1]

$$\begin{array}{c} CH_3 \\ \diagdown_+ \diagup \\ N \\ \diagup \diagdown \\ HOCH_2CH_2 \quad C_2H_4OCOR^{12-1} \end{array} \quad C_2H_4OCOR^{12-1} \quad Cl^-$$

D-2*[1]    mixture of the following compounds
[monoester:diester:triester = 20:55:25 (weight ratio)]

$$\begin{array}{c} CH_3 \quad CH_2CH_2OCOR^{12-1} \\ \diagdown_+ \diagup \\ N \\ \diagup \diagdown \\ HOCH_2CH_2 \quad CH_2CH_2OH \end{array} \quad CH_3SO_4^-$$

$$\begin{array}{c} CH_3 \quad CH_2CH_2OCOR^{12-1} \\ \diagdown_+ \diagup \\ N \\ \diagup \diagdown \\ HOCH_2CH_2 \quad CH_2CH_2OCOR^{12-1} \end{array} \quad CH_3SO_4^-$$

$$\begin{array}{c} CH_3 \quad CH_2CH_2OCOR^{12-1} \\ \diagdown_+ \diagup \\ N \\ \diagup \diagdown \\ R^{12-1}COOCH_2CH_2 \quad CH_2CH_2OCOR^{12-1} \end{array} \quad CH_3SO_4^-$$

D-3*[2]    mixture of the following compounds
[monoester:diester:triester = 20:55:25 (weight ratio)]

$$\begin{array}{c} CH_3 \quad CH_2CH_2OCOR^{12-2} \\ \diagdown_+ \diagup \\ N \\ \diagup \diagdown \\ HOCH_2CH_2 \quad CH_2CH_2OH \end{array} \quad CH_3SO_4^-$$

$$\begin{array}{c} CH_3 \quad CH_2CH_2OCOR^{12-2} \\ \diagdown_+ \diagup \\ N \\ \diagup \diagdown \\ HOCH_2CH_2 \quad CH_2CH_2OCOR^{12-2} \end{array} \quad CH_3SO_4^-$$

TABLE 3-continued

Component (D)

$$\begin{array}{c} CH_3 \quad CH_2CH_2OCOR^{12-2} \\ \diagdown_+ \diagup \\ N \\ \diagup \diagdown \\ R^{12-2}COOCH_2CH_2 \quad CH_2CH_2OCOR^{12-2} \end{array} \quad CH_3SO_4^-$$

Note)
*[1] $R^{12-1}$ represents an alkyl group obtained by eliminating a carboxyl group from hardened beef tallow fatty acid.
*[2] $R^{12-2}$ represents an alkyl group obtained by eliminating a carboxyl group from mixed fatty acids of unhardened beef tallow fatty acid with hardened beef tallow fatty acid at a weight ratio [(former)/(latter)] of 75/25.

TABLE 4

| | Component (E) | |
|---|---|---|
| E-1 | EO adduct of glycerol | (MW 8,900) |
| E-2 | PO/EO (15/85) adduct of glycerol | (MW 10,000) |
| E-3 | PO/EO (10/90) adduct of sorbitol | (MW 15,000) |
| E-4 | PO/EO (2/98) adduct of tetraethylene-pentamine | (MW 20,000) |
| E-5 | PO/EO (5/95) adduct of poly-ethyleneimine (MW 3,000) | (MW 300,000) |

TABLE 5

Component (F)

F-1*[1]
$$\begin{array}{c} CH_3 \\ \diagdown \\ N-CH_2CONHR^{10-1} \\ \diagup \\ CH_3 \end{array}$$

F-2*[2]
$$\begin{array}{c} CH_3 \\ \diagdown \\ N-CH_2CONHR^{10-2} \\ \diagup \\ CH_3 \end{array}$$

F-3*[1]
$$\begin{array}{c} CH_3 \\ \diagdown \\ N-CH_2CH_2CONHR^{10-1} \\ \diagup \\ CH_3 \end{array}$$

F-4*[2]
$$\begin{array}{c} CH_3 \\ \diagdown \\ N-CH_2CH_2CONHR^{10-2} \\ \diagup \\ CH_3 \end{array}$$

F-5
$$\begin{array}{c} CH_3 \\ \diagdown \\ N-CH_2CONHC_{22}H_{45} \\ \diagup \\ CH_3 \end{array}$$

F-6*[3]
$$\begin{array}{c} CH_3 \\ \diagdown \\ N-CH_2CH_2CONHR^{10-3} \\ \diagup \\ CH_3 \end{array}$$

Note)
*[1] $R^{10-1}$ represents an alkyl group obtained by substituting a methylene group for a carboxyl group of hardened beef tallow fatty acid.
*[2] $R^{10-2}$ represents an alkyl group obtained by substituting a methylene group for a carboxyl group of hardened palm oil fatty acid.
*[3] $R^{10-3}$ represents an oleyl group.

(1) Method for the evaluation of softness and elasticity
a) Method for treatment By using a 30-l washing machine, 1.5 kg of a marketed cotton towel and 0.5 kg of cloths made of acrylic fiber (jersy) were repeatedly washed 5 times in hard water of 3.5° DH with the use of a marketed detergent, Attack[R] (mfd. by Kao Corporation), to eliminate the fiber treatment adhering to the fibers. After rinsing the cotton towel and the cloths made of acrylic fiber (jersy) sufficiently, 6 ml of each of the softener compositions as listed in Tables 6 to 11 was added to the washing machine. The cotton towel and the cloths made of acrylic fiber (jersy) were treated in an aqueous solution of each of the softener compositions at 25° C. for 1 minute under stirring.

b) Method for evaluation

The towel and cloths thus treated were air-dried at room temperature and then allowed to stand in a thermohygrostatic room at 25° C. and 65% RH for 24 hours. Then, these towel and cloths were evaluated in softness and elasticity.

The softness and elasticity were evaluated by the paired comparison test with the use of, as a control, the towel or the cloths which had been treated in the same manner as the one described above, except that 10 ml of a softener comprising 15% by weight of di(hardened beef tallow alkyl)dimethylammonium chloride. The results of the evaluation are expressed in accordance with the following criteria.

+3: highly superior to the control in softness or elasticity.

+2: superior to the control in softness or elasticity.

+1: somewhat superior to the control in softness or elasticity.

0: comparable to the control in softness or elasticity.

(2) Method for the evaluation of storage stability

The softener compositions listed in Tables 6 to 11 were stored in a hermetically sealed state at 5, 25 and 50° C. for 20 days (storage test). The appearance and flowability of each softener composition in the sealed state were observed with the naked eye after the completion of the storage test.

In comparison with a composition which had not been subjected to the storage test, those showing no change in appearance or flowability were evaluated as "good", while those suffering from changes were recorded to that effect.

Those which were evaluated as "good" when the appearance and flowability were observed after storing at 5° C. for 20 days, were further stored at 5° C. for 20 days, and then the appearance and flowability were observed. Those showing no change after storing at 5° C. for 40 days were evaluated as "very good".

TABLE 6

| | Softener Composition | | | | | | |
|---|---|---|---|---|---|---|---|
| Ex. no. | Component (A) | Component (B) | Component (C) | Component (D) | Component (E) | Component (F) | Other component |
| 1 | I-1 [25] | — | — | — | — | — | — |
| 2 | I-2 [25] | — | — | — | — | — | — |
| 3 | I-3 [25] | — | — | — | — | — | — |
| 4 | I-4 [25] | — | — | — | — | — | — |
| 5 | I-5 [25] | — | — | — | — | — | — |
| 6 | I-6 [25] | — | — | — | — | — | — |
| 7 | I-5 [23] | — | — | — | — | — | $\mathrm{CH_3} \diagdown \overset{+}{\mathrm{N}} \diagup \mathrm{C_2H_4OH}$ $\mathrm{CH_3} \diagup \diagdown \mathrm{C_2H_4NHCOR^{4-1}}$ $\mathrm{Cl^-}$ [2] $R^{4-1}$ is as defined in Table 1. |
| 8 | I-5 [25] | hardened beef tallow fatty acid [1.5] | isopropanol [2.5] | — | — | — | $C_{12}H_{25}O(CH_2CH_2O)_mH$ (m is 21.0 on av.) [2.5] |
| 9 | I-5 [25] | hardened palm oil fatty acid [1.5] | ethanol [2.5] | — | — | — | — |
| 10 | II-1 [25] | — | — | — | — | — | — |
| 11 | II-2 [25] | — | — | — | — | — | — |
| 12 | II-3 [25] | — | — | — | — | — | — |

TABLE 7

| | Softener Composition | | | | | | |
|---|---|---|---|---|---|---|---|
| Ex. no. | Component (A) | Component (B) | Component (C) | Component (D) | Component (E) | Component (F) | Other component |
| 13 | II-4 [25] | — | — | — | — | — | — |
| 14 | II-5 [25] | — | — | — | — | — | — |
| 15 | II-6 [25] | — | — | — | — | — | — |
| 16 | II-7 [25] | — | — | — | — | — | — |
| 17 | II-8 [25] | — | — | — | — | — | — |

TABLE 7-continued

| | Softener Composition | | | | | | |
|---|---|---|---|---|---|---|---|
| Ex. no. | Component (A) | Component (B) | Component (C) | Component (D) | Component (E) | Component (F) | Other component |
| 18 | II-9 [25] | — | — | — | — | — | — |
| 19 | II-10 [25] | — | — | — | — | — | — |
| 20 | II-4 [24] | — | — | — | — | F-1 [1] | — |
| 21 | II-4 [23] | — | — | — | — | F-2 [2] | — |
| 22 | II-4 [22] | — | — | — | — | F-3 [3] | — |
| 23 | II-4 [23] | — | — | — | — | F-4 [3] | — |
| 24 | II-4 [23] | — | — | — | — | F-5 [3] | — |
| 25 | II-4 [20] | — | ethanol [2.5] | — | — | F-6 [5] | — |
| 26 | II-10 [22] | — | — | — | — | F-4 [3] | — |
| 27 | II-10 [22] | — | isopropanol [2.5] | — | — | F-4 [3] | $C_{12}H_{25}O(CH_2CH_2O)_m H$ m is 21.0 on av. [2.5] |

TABLE 8

| | Softener Composition | | | | | | |
|---|---|---|---|---|---|---|---|
| Ex. no. | Component (A) | Component (B) | Component (C) | Component (D) | Component (E) | Component (F) | Other component |
| 28 | I-5 [17] | — | — | D-1 [8] | — | — | — |
| 29 | I-5 [17] | hardened beef tallow fatty acid [1] | isopropanol [2] | D-2 [8] | — | — | — |
| 30 | I-5 [17] | — | isopropanol [2] | D-3 [8] | — | — | — |
| 31 | I-5 [12] | — | isopropanol [3] | D-3 [13] | — | — | — |
| 32 | II-9 [17] | — | — | D-1 [8] | — | — | — |
| 33 | II-9 [17] | hardened beef tallow fatty acid [1] | isopropanol [2] | D-2 [8] | — | — | — |
| 34 | II-9 [17] | — | isopropanol [2] | D-3 [8] | — | — | — |
| 35 | II-9 [12] | — | isopropanol [3] | D-3 [13] | — | — | — |
| 36 | II-10 [9] | — | — | D-3 [8] | — | F-4 [3] | — |
| 37 | II-5 [25] | — | — | — | E-1 [1.5] | — | — |
| 38 | II-5 [25] | — | — | — | E-2 [1.5] | — | — |

TABLE 9

| | Softener Composition | | | | | | |
|---|---|---|---|---|---|---|---|
| Ex. no. | Component (A) | Component (B) | Component (C) | Component (D) | Component (E) | Component (F) | Other component |
| 39 | I-5 [25] | — | — | — | E-3 [1.5] | — | — |
| 40 | I-5 [25] | — | — | — | E-4 [1.5] | — | — |
| 41 | I-5 [25] | — | — | — | E-5 [1.5] | — | — |
| 42 | II-9 [25] | hardened beef tallow fatty acid [1.5] | isopropanol [2.5] | — | E-4 [1.5] | — | — |
| 43 | II-9 [25] | — | — | — | E-1 [1.5] | — | — |
| 44 | II-9 [25] | — | — | — | E-2 [1.5] | — | — |
| 45 | II-9 [25] | — | — | — | E-3 [1.5] | — | — |
| 46 | II-9 [25] | — | — | — | E-4 [1.5] | — | — |
| 47 | II-9 [25] | — | — | — | E-5 [1.5] | — | — |
| 48 | II-9 [25] | hardened beef tallow fatty acid [1.5] | isopropanol [2.5] | — | E-4 [1.5] | — | — |
| 49 | II-10 [22] | — | — | — | E-4 [1.5] | F-4 [3] | — |

TABLE 10

| Comp. Ex. no. | Component (A) | Component (B) | Component (C) | Component (D) | Component (E) | Component (F) | Other component | |
|---|---|---|---|---|---|---|---|---|
| 1 | — | — | — | — | — | — | compd. (i) | [25] |
| 2 | — | — | — | — | — | — | compd. (ii) | [25] |
| 3 | — | — | — | — | — | — | compd. (iii) | [25] |
| 4 | — | — | — | — | — | — | compd. (iv) | [25] |
| 5 | — | — | — | — | — | — | compd. (v) | [25] |
| 6 | — | — | isopropanol [2] | — | — | F-4 [2] | compd. (i) | [23] |
| 7 | — | — | — | — | — | F-4 [3] | compd. (iv) | [22] |
| 8 | — | — | isopropanol [5] | D-2 [25] | — | — | — | |
| 9 | — | — | isopropanol [5] | D-2 [23.5] | E-4 [1.5] | — | — | |
| 10 | — | hardened beef tallow fatty acid [1.5] | — | — | — | — | compd. (i) | [23.5] |
| 11 | — | hardened beef tallow fatty acid [1.5] | — | — | — | — | compd. (ii) | [23.5] |
| 12 | — | hardened palm oil fatty acid [1.5] | — | — | — | — | compd. (iii) | [23.5] |

TABLE 11

| Comp. Ex. no. | Component (A) | Component (B) | Component (C) | Component (D) | Component (E) | Component (F) | Other component | |
|---|---|---|---|---|---|---|---|---|
| 13 | — | hardened palm oil fatty acid [1.5] | — | — | — | — | compd. (iv) | [23.5] |
| 14 | — | hardened palm oil fatty acid [1.5] | — | — | — | — | compd. (v) | [23.5] |
| 15 | — | hardened beef tallow fatty acid [1.5] | isopropanol [2.5] | — | — | — | compd. (i) | [23.5] |
| 16 | — | hardened beef tallow fatty acid [1.5] | isopropanol [2.5] | — | — | — | compd. (ii) | [23.5] |
| 17 | — | hardened palm oil fatty acid [1.5] | ethanol [2.5] | — | — | — | compd. (iii) | [23.5] |
| 18 | — | hardened palm oil fatty acid [1.5] | ethanol [2.5] | — | — | — | compd. (iv) | [23.5] |
| 19 | — | hardened palm oil fatty acid [1.5] | ethanol [2.5] | — | — | — | compd. (v) | [23.5] |

TABLE 12

| | Evaluation of performance | | Storage stability | | |
|---|---|---|---|---|---|
| Ex. no. | Softness | Elasticity | 5° C. | 25° C. | 50° C. |
| 1 | +1 | +1 | good | good | good |
| 2 | 0 | +1 | good | good | good |
| 3 | 0 | +1 | good | good | good |
| 4 | 0 | +1 | good | good | good |
| 5 | +1 | +1 | good | good | good |
| 6 | +1 | +1 | good | good | good |
| 7 | +2 | +1 | good | good | good |
| 8 | +1 | +1 | good | good | good |
| 9 | +1 | +1 | good | good | good |
| 10 | +1 | +1 | good | good | good |
| 11 | +1 | +1 | good | good | good |
| 12 | 0 | +1 | good | good | good |
| 13 | +1 | +1 | good | good | good |
| 14 | +1 | +1 | good | good | good |
| 15 | 0 | +1 | good | good | good |
| 16 | +1 | +1 | good | good | good |
| 17 | 0 | +1 | good | good | good |
| 18 | +1 | +1 | good | good | good |

TABLE 12-continued

| Ex. no. | Evaluation of performance | | Storage stability | | |
|---|---|---|---|---|---|
| | Softness | Elasticity | 5° C. | 25° C. | 50° C. |
| 19 | +1 | +1 | good | good | good |
| 20 | +1 | +2 | good | good | good |
| 21 | +1 | +2 | good | good | good |
| 22 | +1 | +2 | good | good | good |
| 23 | +1 | +2 | good | good | good |
| 24 | +1 | +2 | good | good | good |
| 25 | +1 | +2 | good | good | good |

TABLE 13

| Ex. no. | Evaluation of performance | | Storage stability | | |
|---|---|---|---|---|---|
| | Softness | Elasticity | 5° C. | 25° C. | 50° C. |
| 26 | +1 | +2 | good | good | good |
| 27 | +1 | +2 | good | good | good |
| 28 | +1 | +3 | good | good | good |
| 29 | +1 | +3 | good | good | good |
| 30 | +1 | +3 | good | good | good |
| 31 | +1 | +3 | good | good | good |
| 32 | +1 | +3 | good | good | good |
| 33 | +1 | +3 | good | good | good |
| 34 | +1 | +3 | good | good | good |
| 35 | +1 | +3 | good | good | good |
| 36 | +1 | +3 | good | good | good |
| 37 | +1 | +1 | very good | good | good |
| 38 | +1 | +1 | very good | good | good |
| 39 | +1 | +1 | very good | good | good |
| 40 | +1 | +1 | very good | good | good |
| 41 | +1 | +1 | very good | good | good |
| 42 | +1 | +1 | very good | good | good |
| 43 | +1 | +1 | very good | good | good |
| 44 | +1 | +1 | very good | good | good |
| 45 | +1 | +1 | very good | good | good |
| 46 | +1 | +1 | very good | good | good |
| 47 | +1 | +1 | very good | good | good |
| 48 | +1 | +1 | very good | good | good |
| 49 | +1 | +2 | very good | good | good |

TABLE 14

| Comp. Ex. no. | Evaluation of performance | | Storage stability | | |
|---|---|---|---|---|---|
| | Softness | Elasticity | 5° C. | 25° C. | 50° C. |
| 1 | 0 | 0 | thickened | good | thickened |
| 2 | 0 | 0 | thickened | good | thickened |
| 3 | 0 | 0 | thickened | good | thickened |
| 4 | 0 | 0 | thickened | good | thickened |
| 5 | 0 | 0 | thickened | good | thickened |
| 6 | 0 | 0 | gelled | good | thickened |
| 7 | 0 | 0 | thickened | good | thickened |
| 8 | 0 | 0 | gelled | thickened | thickened |
| 9 | 0 | 0 | thickened | good | thickened |
| 10 | 0 | 0 | thickened | good | thickened |
| 11 | 0 | 0 | thickened | good | thickened |
| 12 | 0 | 0 | thickened | good | thickened |
| 13 | 0 | 0 | thickened | good | thickened |
| 14 | 0 | 0 | thickened | good | thickened |
| 15 | 0 | 0 | gelled | good | thickened |
| 16 | 0 | 0 | thickened | good | thickened |
| 17 | 0 | 0 | gelled | good | gelled |
| 18 | 0 | 0 | thickened | good | thickened |
| 19 | 0 | 0 | thickened | good | thickened |

As the above Tables 12 to 14 clearly show, each of the aqueous fabric softener compositions of the present invention suffers from little change in appearance or flowability with the lapse of time and thus shows excellent stability. Further, the softnesses and elasticities of the towel and the cloths made of acrylic fiber (jersey) treated with the aqueous fabric softener compositions of the present invention are comparable or superior to the control.

Example 50 and Comparative Examples 20 and 21

The quaternary ammonium salt (I-6), the compound (v) or the compound (vi) in a molten state, each adjusted to a final concentration of 20% by weight in an emulsion composition comprising deionized water as an aqueous phase, was slowly added to deionized water heated to 60° C. under stirring to thereby give a homogeneous emulsion. Then, $CaCl_2$ was added in such an amount as to give a final concentration of 0.24 by weight in the composition. Then, the pH value of the emulsion was adjusted to 5 by adding an appropriate amount of NaOH or HCl. After cooling, a softener composition was obtained.

The softener composition thus obtained was introduced into a container, sealed and stored at 50° C. for 20 days. The appearance of the softener - composition after storage, the hydrolysis ratio of the softening base after storage and changes in the softening performance before and after the storage were evaluated.

The softness was evaluated by the following method as a sensory test with 10 skilled panelists.

Namely, a cotton towel treated with the composition comprising the quaternary ammonium salt (I-6) as a softening base before the storage was employed as a control and cotton towels treated with the softener compositions before and after the storage were evaluated with respect to softness by the paired comparison test. The evaluation was made in accordance with the following criteria.

0: comparable to the control.

−1: rather inferior to the control.

−2: inferior to the control.

−3: clearly inferior to the control.

Table 15 shows the results.

TABLE 15

| | Softening base | Appearance | Hydrolysis ratio*1 (%) | Softness before storage | Softness after storage |
|---|---|---|---|---|---|
| Ex. 50 | CH₃\⁺/C₂H₄OCOR³⁻² N CH₃/\C₂H₄NHCOR⁴⁻² Cl⁻ (I-6)*² | good | ≦5 | control | 0 |
| Comp. Ex. 20 | CH₃\⁺/C₂H₄OCOR³⁻² N CH₃/\C₃H₆NHCOR⁴⁻² Cl⁻ compd. (v)*² | gelation | ≦5 | −1 | −2 |
| Comp. Ex. 21 | C₂H₄OCOR³⁻² / CH₃N .HCl \ C₃H₆NHCOR⁴⁻² compd. (vi)*² | separation | 35 | −1 | −3 |

Note)

*¹calculated from the area ratio of $-CH_2-OCR^{3-2}$ (with C=O) to $-CH_2-OH$ in $^1H$—NMR.

*²$R^{3-2}$ and $R^{4-2}$ represent each an alkyl group obtained by eliminating a carboxyl group from hardened palm oil fatty acid.

These results indicate that the softener composition of the present invention is highly excellent in storage stability and exhibits an excellent softening performance.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim is:

1. An aqueous fabric softener composition comprising 3 to 40% by weight, based on the total weight of the composition, of component (A) consisting of at least one quaternary ammonium salt represented by the following formula (I), and water:

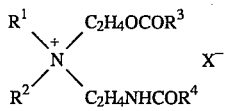

(I)

wherein $R^1$ and $R^2$ may be the same or different from each other and each represents an alkyl or hydroxyalkyl group having 1 to 4 carbon atoms; $R^3$ and $R^4$ may be the same or different from each other and each represents a linear or branched alkyl group derived from hardened palm oil or hardened beef tallow fatty acid; and $X^-$ represents an anion group.

2. The aqueous fabric softener composition according to claim 1, wherein $R^1$ and $R^2$ each represents a methyl group, and $R^3CO$ and $R^4CO$ each represents an acyl group derived from hardened beef tallow.

3. The aqueous fabric softener composition according to claim 1, wherein component (A) consists of a mixture of a quaternary ammonium salt represented by formula (I) and a quaternary ammonium salt represented by the following formula (II)

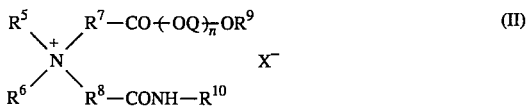

(II)

wherein $R^5$ and $R^6$ may be the same or different from each other and each represents an alkyl or hydroxyalkyl group having 1 to 4 carbon atoms; $R^7$ and $R^8$ may be the same or different from each other and each represents an alkylene, alkenylene or hydroxyalkylene group having 1 to 5 carbon atoms; $R^9$ and $R^{10}$ may be the same or different from each other and each represents a linear or branched alkyl or alkenyl group having 8 to 36 carbon atoms; Q represents an alkylene group having 2 to 6 carbon atoms; $X^-$ represents an anion group; n is a number of from 0 to 10; and each Q may be the same or different from one another.

4. The aqueous fabric softener composition according to claim 1, which further comprises a linear or branched, saturated or unsaturated fatty acid having 8 to 36 carbon atoms as component (B), wherein the amount of component (B) is not more than 100% by weight based on the weight of component (A).

5. The aqueous fabric softener composition according to claim 1, which further comprises a monohydric alcohol having 1 to 4 carbon atoms as component (C), wherein the amount of component (C) is not more than 60% by weight based on the weight of component (A).

6. The aqueous fabric softener composition according to claim 1, which further comprises not more than 40% by weight, based on the total weight of the composition, of a quaternary ammonium salt represented by the following formula (III) as component (D), wherein the total amount of component (A) and component (D) is from 3 to 50% by weight based on the total weight of the composition:

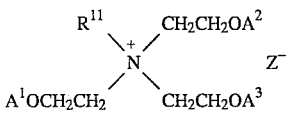 (III)

wherein $R^{11}$ represents an alkyl or hydroxyalkyl group having 1 to 4 carbon atoms; $A^1$, $A^2$ and $A^3$ may be the same or different from one another and each represents a hydrogen atom or a group represented by the formula: $R^{12}CO-$, wherein $R^{12}$ represents a linear or branched alkyl or alkenyl group having 7 to 35 carbon atoms, and at least one of $A^1$, $A^2$ and $A^3$ is a group represented by the formula: $R^{12}CO-$, wherein $R^{12}$ is as defined above; and $Z^-$ represents an anion group.

7. The aqueous fabric softener composition according to claim 1, which further comprises 0.5 to 5% by weight, based on the total weight of the composition, of a polyester compound having a weight average molecular weight of from 5,000 to 2,000,000, wherein oxyethylene groups are present in amount of 55% by weight or more based on the molecular weight of the polyether compound, as component (E), wherein the weight ratio of component (E) to component (A) is from 1/100 to 1/2.5, and the total amount of component (A) and component (E) is from 4 to 45% by weight based on the total weight of the composition.

8. The aqueous fabric softener according to claim 7, wherein the polyether compound is obtained by adding ethylene oxide and, optionally, at least one of propylene oxide and trimethylene oxide with a compound selected from the group consisting of polyhydric alcohols, polyhydric phenols, and polyamines.

9. The aqueous fabric softener composition according to claim 1, which further comprises an amidoamine represented by the following formula (IV) or an acid salt thereof as component (F), wherein the amount of component (F) is not more than 110% by weight based on the weight of component (A):

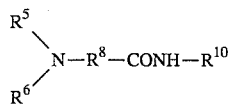 (IV)

wherein $R^5$ and $R^6$ may be the same or different from each other and each represents an alkyl or hydroxyalkyl group having 1 to 4 carbon atoms; $R^8$ represents an alkylene, alkenylene or hydroxyalkylene group having 1 to 5 carbon atoms; and $R^{10}$ represents a linear or branched alkyl or alkenyl group having 8 to 36 carbon atoms.

10. The aqueous fabric softener composition according to claim 1, which further comprises at least one compound selected from the group consisting of compounds represented by the following formulas

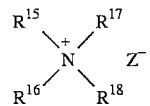 (XVII-1)

wherein $R^{15}$ and $R^{16}$ may be the same or different from each other and each represents a linear or branched, alkyl, alkenyl or 2-hydroxyalkyl group having 10 to 24 carbon atoms; $R^{17}$ represents an alkyl or hydroxyalkyl group having 1 to 3 carbon atoms, a benzyl group or a group represented by the formula: $-(C_2H_4O)_mH$ (wherein m is a number of from 1 to 3); $R^{18}$ represents a hydrogen atom, an alkyl or hydroxyalkyl group having 1 to 3 carbon atoms, a benzyl group or a group represented by the formula: $-(C_2H_4O)_mH$ (wherein m is as defined above); and $Z^-$ is as defined above,

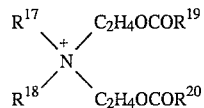 (XVII-2)

wherein $R^{17}$, $R^{18}$ and $Z^-$ are each as defined above; and $R^{19}$ and $R^{20}$ may be the same or different from each other and each represents a linear or branched alkyl, alkenyl or 2-hydroxyalkyl group having 9 to 23 carbon atoms,

 (XVII-3)

wherein $R^{17}$, $R^{18}$, $R^{19}$ and $Z^-$ are each as defined above,

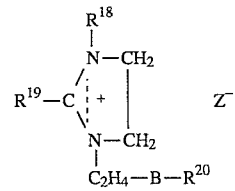 (XVII-4)

wherein $R^{18}$, $R^{19}$, $R^{20}$ and $Z^-$ are each as defined above; and B represents a group represented by the formula: $-OCO-$ or the formula: $-NHCO-$,

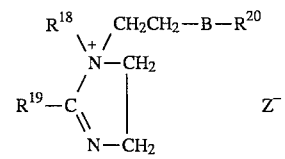 (XVII-5)

wherein $R^{18}$, $R^{19}$, $R^{20}$, B and $Z^-$ are each as defined above,

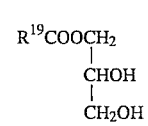 (XVII-6)

wherein $R^{19}$ is as defined above,

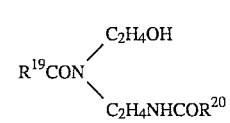 (XVII-7)

wherein $R^{19}$ and $R^{20}$ are each as defined above,

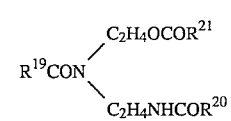 (XVII-8)

wherein $R^{19}$ and $R^{20}$ are each as defined above; and $R^{21}$ represents a linear or branched, alkyl, alkenyl or 2-hydroxyalkyl group having 9 to 23 carbon atoms, and

 (XVII-9)

wherein $R^{22}$ represents a linear or branched, alkyl or alkenyl group having 10 to 24 carbon atoms.

11. The aqueous fabric softener composition according to claim 1, which further comprises a quaternary ammonium salt represented by the following formula (XX) as component (H), wherein the amount of component (H) is not more than 110% by weight based on the weight of component (A):

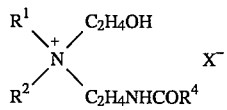 (XX)

wherein $R^1$, $R^2$, $R^4$ and $X^-$ are each as defined above.

12. A method for imparting softness and elasticity to fibers comprising treating fibers with the composition of claim 1.

13. A method for imparting softness and elasticity to fibers comprising treating fibers with the composition of claim 3.

* * * * *